(12) United States Patent
Briganti et al.

(10) Patent No.: US 12,391,989 B2
(45) Date of Patent: Aug. 19, 2025

(54) METHODS OF TREATMENT, GENETIC SCREENING, AND DISEASE MODELS FOR HEART CONDITIONS ASSOCIATED WITH RBM20 DEFICIENCY

(71) Applicants: The Board of Trustees of the Leland Stanford Junior University, Stanford, CA (US); EUROPEAN MOLECULAR BIOLOGY LABORATORY, Heidelberg (DE)

(72) Inventors: Francesca Briganti, Palo Alto, CA (US); Lars M. Steinmetz, Palo Alto, CA (US); Han Sun, Mountain View, CA (US); Wu Wei, Palo Alto, CA (US)

(73) Assignees: European Molecular Biology Laboratory, Heidelberg (DE); The Board of Trustees of the Leland Stanford Junior University, Stanford, CA (US)

( * ) Notice: Subject to any disclaimer, the term of this patent is extended or adjusted under 35 U.S.C. 154(b) by 1118 days.

(21) Appl. No.: 17/289,528

(22) PCT Filed: Oct. 25, 2019

(86) PCT No.: PCT/US2019/058169
§ 371 (c)(1),
(2) Date: Apr. 28, 2021

(87) PCT Pub. No.: WO2020/092171
PCT Pub. Date: May 7, 2020

(65) Prior Publication Data
US 2021/0395822 A1  Dec. 23, 2021

Related U.S. Application Data

(60) Provisional application No. 62/753,034, filed on Oct. 30, 2018.

(51) Int. Cl.
*C12Q 1/6883* (2018.01)
*A61K 31/203* (2006.01)
*A61P 9/04* (2006.01)

(52) U.S. Cl.
CPC .......... *C12Q 1/6883* (2013.01); *A61K 31/203* (2013.01); *A61P 9/04* (2018.01); *C12Q 2600/156* (2013.01)

(58) Field of Classification Search
CPC ............ C12Q 1/6883; C12Q 2600/156; C12Q 2600/158; A61P 9/04; A61K 31/203
See application file for complete search history.

(56) References Cited

U.S. PATENT DOCUMENTS

2013/0029866 A1   1/2013   Sun et al.

FOREIGN PATENT DOCUMENTS

| WO | 2018002215 A1 | 1/2018 |
| WO | 2018005546 A1 | 1/2018 |
| WO | 2018057790 A1 | 3/2018 |

OTHER PUBLICATIONS

Posafalvi, A. Matters of the heart: genetic and molecular characterisation of cardiomyopathies. Thesis (particularly Chapter 2.1), University of Groningen. (Year: 2015).*

(Continued)

*Primary Examiner* — Diana B Johannsen
(74) *Attorney, Agent, or Firm* — Jenny L. Buchbinder; Bozicevic, Field & Francis LLP

(57) ABSTRACT

Methods of treatment, genetic screening, and disease models for heart conditions associated with RBM20 deficiency are disclosed. In particular, methods of treating heart conditions associated with RBM20 deficiency, including RBM20-dependent dilated cardiomyopathy and heart failure with compounds that upregulate expression of RBM20, such as all-trans retinoic acid are provided. Also disclosed are methods of genetic screening to detect the presence of a P633L (Continued)

mutation in RBM20 in order to identify individuals having a genetic predisposition to developing RBM20-dependent DCM. Induced pluripotent stem cell-derived cardiomyocytes (IPSC-CMs) produced by differentiation of IPSCs comprising at least one RBM20 allele encoding a P633L mutation and methods of using them in screening for therapeutics for treating RBM20-dependent DCM are also disclosed.

15 Claims, 37 Drawing Sheets

Specification includes a Sequence Listing.

(56) References Cited

OTHER PUBLICATIONS

Duong, G. et al. Journal of Biological Methods 43(e):e78 (pp. 1-7) (Sep. 2017). (Year: 2017).*
McMurray, J. et al. The European Journal of Heart Failure 7:710-721. (Year: 2005).*
Yang, N.I. et al. Circulation 134(Suppl 1): Abstract No. 20438. (Nov. 2016). (Year: 2016).*
Paiva, S.A.R. et al. Journal of Nutrition 135:2326-2328. (Year: 2005).*
Rego et al., (2017) "High Frequency Actionable Pathogenic Exome Mutations in an Average-Risk Cohort." BioRxiv. 1-28.
Silva et al., (2017) "Cardiac Remodeling Induced by All-Trans Retinoic Acid is Detrimental in Normal Rats." Cellular Physiology and Biochemistry, 43(4):1449-1459.
Siu et al., (2002) "Transient Dilated Cardiomyopathy in a Newborn Exposed to Idarubicin and All-Trans-Retinoic Acid (ATRA) Early in the Second Trimester of Pregnancy. International." Journal of Gynecological Cancer, 12(4):399-402.
Wang et al., (2002) "Effects of All-Trans Retinoic Acid on Angiotensin II-Induced Myocyte Hypertrophy." Journal of Applied Physiology, 92(5):2162-2168.
Maatz et al., (2014) "RNA-binding protein RBM20 represses splicing to orchestrate cardiac pre-mRNA processing." J. Clin. Invest., 124:3419-3430.
Beraldi et al., (2014) "Rbm20-deficient cardiogenesis reveals early disruption of RNA processing and sarcomere remodeling establishing a developmental etiology for dilated cardiomyopathy.", Hum. Mol. Genet., 23:3779-3791.
McNally et al., (2017) "Dilated Cardiomyopathy: Genetic Determinants and Mechanisms.", Circ Res., 121:731-748.
Li et al., (2010) "Identification of Novel Mutations in RBM20 in Patients with Dilated Cardiomyopathy.", Clin Transl Sci., 3:90-97.
Brauch et al., (2009) "Mutations in ribonucleic acid binding protein gene cause familial dilated cardiomyopathy.", J Am Coll Cardiol., 54:930-941.
Guo et al., (2012) "RBM20, a gene for hereditary cardiomyopathy, regulates titin splicing.", Nat Med., 18:766-773.
Li et al., (2013) "Rbm20 regulates titin alternative splicing as a splicing repressor.", Nucleic Acids Res., 41:2659-2672.
Murayama et al., (2018) "Phosphorylation of the RSRSP stretch is critical for splicing regulation by RNA-Binding Motif Protein 20 (RBM20) through nuclear localization.", Sci Rep., 8:8970.

* cited by examiner

| | | |
|---|---|---|
| 555 | LEHFMLERPRSRSPINH | Oryzias lapites |
| 627 | ADRYGPERPRSRSPMSR | Mus musculus |
| 628 | ADRYGPERPRSRSPMSR | Rattus norvegicus |
| 512 | ADRYGPERPRSRSPVSR | Canis lupus familiaris |
| 589 | ADRYGPERPRSRSPVSR | Macaca mulatta |
| 628 | ADRYGPERPRSRSPVSR | Homo sapiens |
| 628 | ADRYGPERPRSRSPVSR | Pan troglodytes |

FIG. 1C

RBM20 wt ——— P R S R S ———
RBM20-scr ——— L Q A H G ———

FIG. 7A

SEQUENCE LISTING

```
<160> NUMBER OF SEQ ID NOS: 18

<210> SEQ ID NO 1
<211> LENGTH: 25
<212> TYPE: DNA
<213> ORGANISM: Artificial Sequence
<220> FEATURE:
<223> OTHER INFORMATION: Forward Guide 2 oligonucleoitide for sgRNA
      cloning
<220> FEATURE:
<221> NAME/KEY: source
<222> LOCATION: (1)..(25)
<223> OTHER INFORMATION: sequence is synthesized

<400> SEQUENCE: 1
caccgctcac cggactacga gaccg                                         25

<210> SEQ ID NO 2
<211> LENGTH: 25
<212> TYPE: DNA
<213> ORGANISM: Artificial Sequence
<220> FEATURE:
<223> OTHER INFORMATION: Reverse Guide 2 oligonucleoitide for sgRNA
      cloning
<220> FEATURE:
<221> NAME/KEY: source
<222> LOCATION: (1)..(25)
<223> OTHER INFORMATION: sequence is synthesized

<400> SEQUENCE: 2
aaaccggtct cgtagtccgg tgagc                                         25

<210> SEQ ID NO 3
<211> LENGTH: 127
<212> TYPE: DNA
<213> ORGANISM: Artificial Sequence
<220> FEATURE:
<223> OTHER INFORMATION: R634Q KI donor polynucleotide
<220> FEATURE:
<221> NAME/KEY: source
<222> LOCATION: (1)..(127)
<223> OTHER INFORMATION: sequence is synthesized

<400> SEQUENCE: 3
tgtgggacct cggggagagt gaccggctca ccggactacg agactgcggc ctttctgggc   60
catatctgtg agggagccaa ggagcaggat ttagaatctt cacacctccc atcccacccc  120
acccaca                                                            127

<210> SEQ ID NO 4
```

```
<211> LENGTH: 22
<212> TYPE: DNA
<213> ORGANISM: Artificial Sequence
<220> FEATURE:
<223> OTHER INFORMATION: RBM20 forward PCR primer
<220> FEATURE:
<221> NAME/KEY: source
<222> LOCATION: (1)..(22)
<223> OTHER INFORMATION: sequence is synthesized

<400> SEQUENCE: 4
ctggactagg gcaatcttgc cc                                              22

<210> SEQ ID NO 5
<211> LENGTH: 22
<212> TYPE: DNA
<213> ORGANISM: Artificial Sequence
<220> FEATURE:
<223> OTHER INFORMATION: RBM20 reverse PCR primer
<220> FEATURE:
<221> NAME/KEY: source
<222> LOCATION: (1)..(22)
<223> OTHER INFORMATION: sequence is synthesized

<400> SEQUENCE: 5
ctcattctgc ttggccttgg cg                                              22

<210> SEQ ID NO 6
<211> LENGTH: 17
<212> TYPE: PRT
<213> ORGANISM: Oryzias latipes

<400> SEQUENCE: 6

Leu Glu His Phe Met Leu Glu Arg Pro Arg Ser Arg Ser Pro Ile Asn
1               5                   10                  15

His

<210> SEQ ID NO 7
<211> LENGTH: 17
<212> TYPE: PRT
<213> ORGANISM: Mus musculus

<400> SEQUENCE: 7

Ala Asp Arg Tyr Gly Pro Glu Arg Pro Arg Ser Arg Ser Pro Met Ser
1               5                   10                  15

Arg

<210> SEQ ID NO 8
<211> LENGTH: 17
<212> TYPE: PRT
<213> ORGANISM: Homo sapiens

<400> SEQUENCE: 8

Ala Asp Arg Tyr Gly Pro Glu Arg Pro Arg Ser Arg Ser Pro Val Ser
1               5                   10                  15

Arg

<210> SEQ ID NO 9
<211> LENGTH: 21
<212> TYPE: DNA
<213> ORGANISM: Artificial Sequence
<220> FEATURE:
<223> OTHER INFORMATION: RBM20 cDNA template sequence

<400> SEQUENCE: 9
```
aggccgcggt ctcgtagtcc g                          21

<210> SEQ ID NO 10
<211> LENGTH: 7
<212> TYPE: PRT
<213> ORGANISM: Artificial Sequence
<220> FEATURE:
<223> OTHER INFORMATION: translation of RBM20 cDNA template sequence

<400> SEQUENCE: 10

Arg Pro Arg Ser Arg Ser Pro
1               5

<210> SEQ ID NO 11
<211> LENGTH: 21
<212> TYPE: DNA
<213> ORGANISM: Artificial Sequence
<220> FEATURE:
<223> OTHER INFORMATION: clone 3B with P633L mutation

<400> SEQUENCE: 11
aggctgcggt ctcgtagtcc g                          21

<210> SEQ ID NO 12
<211> LENGTH: 7
<212> TYPE: PRT
<213> ORGANISM: Artificial Sequence
<220> FEATURE:
<223> OTHER INFORMATION: Clone 3B peptide with P633L mutation

<400> SEQUENCE: 12

Arg Leu Arg Ser Arg Ser Pro
1               5

<210> SEQ ID NO 13
<211> LENGTH: 21
<212> TYPE: DNA
<213> ORGANISM: Artificial Sequence
<220> FEATURE:
<223> OTHER INFORMATION: Clone 34 with R634Q mutation

<400> SEQUENCE: 13
aggccgcagt ctcgtagtcc g                          21

<210> SEQ ID NO 14
<211> LENGTH: 7
<212> TYPE: PRT
<213> ORGANISM: Artificial Sequence
<220> FEATURE:
<223> OTHER INFORMATION: Clone 34 R634Q peptide

<400> SEQUENCE: 14

Arg Pro Gln Ser Arg Ser Pro
1               5

<210> SEQ ID NO 15
<211> LENGTH: 18
<212> TYPE: DNA
<213> ORGANISM: Artificial Sequence
<220> FEATURE:
<223> OTHER INFORMATION: Clone 23 S635FS

<400> SEQUENCE: 15
ggccgcatct gtagtccg                              18

<210> SEQ ID NO 16

```
<211> LENGTH: 4
<212> TYPE: PRT
<213> ORGANISM: Artificial Sequence
<220> FEATURE:
<223> OTHER INFORMATION: Clone 23 S635FS peptide

<400> SEQUENCE: 16

Arg Pro His Leu
1

<210> SEQ ID NO 17
<211> LENGTH: 5
<212> TYPE: PRT
<213> ORGANISM: Artificial Sequence
<220> FEATURE:
<223> OTHER INFORMATION: RBM20 wt peptide

<400> SEQUENCE: 17

Pro Arg Ser Arg Ser
1               5

<210> SEQ ID NO 18
<211> LENGTH: 5
<212> TYPE: PRT
<213> ORGANISM: Artificial Sequence
<220> FEATURE:
<223> OTHER INFORMATION: RBM20-scr peptide

<400> SEQUENCE: 18

Leu Gln Ala His Gly
1               5
```

METHODS OF TREATMENT, GENETIC SCREENING, AND DISEASE MODELS FOR HEART CONDITIONS ASSOCIATED WITH RBM20 DEFICIENCY

STATEMENT REGARDING FEDERALLY SPONSORED RESEARCH OR DEVELOPMENT

This invention was made with Government support under contracts HG000205 and TR001085 awarded by the National Institutes of Health. The Government has certain rights in the invention.

INCORPORATION BY REFERENCE OF SEQUENCE LISTING PROVIDED AS A TEXT FILE

A Sequence Listing is provided herewith as a text file, "STAN-1549_S18-210_ST25," created on Nov. 1, 2024 and having a size of 4,585 bytes. The contents of the text file are incorporated by reference herein in their entirety.

BACKGROUND OF THE INVENTION

Dilated cardiomyopathy (DCM) is a leading cause of heart failure (Yancy et al. (2013) Circulation 128:1810-1852) and the most common indication for heart transplantation (Japp et al. (2016) J. Am. Coll. Cardiol. 67:2996-3010). Prevalence is estimated at 1 in 250, and 30-50% of the cases are familial (McNally et al. (2017) Circ Res. 121:731-748, Wilcox et al. (2018) Curr. Opin. Cardiol. 33(3):354-362). DCM is characterized by enlargement of the left ventricle and reduced systolic function (Hershberger et al. (2010) Genet. Med. 12:655-667). The five year survival rate after diagnosis is close to 50% (Li et al. (2010) Clin. Transl. Sci. 3:90-97). Therapeutic strategies are limited to managing DCM symptoms. Heart transplantation is considered when a diagnosis of heart failure is assigned. Access to heart transplantation is limited. Despite an improvement of the outcome of transplantation over the past 20 years, development of comorbidity is still a serious problem after transplantation and the 10 year survival rate is just above 50% (Lund et al. (2017) J. Heart Lung Transplant 36:1037-1046).

DCM is a complex disease characterized by variable etiology, clinical presentation, and age of onset (Hershberger et al. (2013) Nat. Rev. Cardiol. 10:531-547). A substantial effort has been made in the past few years to identify the genetic causes of DCM (Kinnamon et al. (2017) Circ. Cardiovasc. Genet. 10(6) pii: e001826). This effort uncovered complex molecular pathways whose perturbation leads to the pathogenesis of DCM. However, genetic mutations and molecular data have not played a major role in the identification of putative therapeutic strategies. This suggests a need for a greater molecular and cellular understanding of the disease, essential for designing coherent therapeutic strategies and for finding a cure.

RBM20 regulates heart-specific splicing of genes essential for muscle function (Maatz et al. (2014) J. Clin. Invest. 124:3419-3430, Beraldi et al. (2014) Hum. Mol. Genet. 23:3779-3791). Mutations in RBM20 are responsible for approximately 3-5% of familial DCM cases and are associated with early onset, end-stage heart failure (also in younger patients), and increased incidence of sudden death. There remains a need for better methods of genetic screening and treatment for RBM20-dependent DCM.

SUMMARY OF THE INVENTION

The invention relates to methods of treating heart conditions associated with RBM20 deficiency, including RBM20-dependent dilated cardiomyopathy (DCM) and heart failure with compounds that upregulate expression of RBM20, such as all-trans retinoic acid. The invention further relates to methods of genetic screening for the presence of a P633L mutation in RBM20 in order to determine if a subject has a genetic predisposition to developing RBM20-dependent DCM. In addition, the invention relates to induced pluripotent stem cell (IPSC)-derived cardiomyocytes (IPSC-CMs) produced by differentiation of IPSCs comprising at least one RBM20 allele encoding a P633L mutation and their use in screening for therapeutics for treating RBM20-dependent DCM.

In one aspect, the invention includes a method of treating a subject for a heart conditions associated with RBM20 deficiency, the method comprising administering a therapeutically effective amount of all-trans retinoic acid (ATRA) to the subject. In certain embodiments, the heart contion associated with RBM20 deficiency is RBM20-dependent dilated cardiomyopathy (DCM) or heart failure.

By "therapeutically effective dose or amount" of ATRA is intended an amount that, when administered as described herein, brings about a positive therapeutic response with respect to treatment of an individual for a heart condition associated with RBM20 deficiency (e.g., RBM20-dependent dilated cardiomyopathy or heart failure). By "positive therapeutic response" is intended that the individual undergoing treatment exhibits an improvement in one or more symptoms of the heart condition associated with RBM20 deficiency (e.g., RBM20-dependent dilated cardiomyopathy or heart failure), such as reduced RBM20-mediated splicing defects (e.g., reduced aberrant splicing of TTN transcripts), improved calcium handling (e.g., calcium transients with increased rate of calcium influx (i.e., reduction of calcium influx time)), and increased contractile capacity of cardiomyocytes. Additionally, a therapeutically effective dose or amount may increase expression of RBM20.

The subject may be treated either prophylactically (e.g., to prevent heart damage in individuals with a mutant RBM20 allele) or therapeutically (e.g., to treat RBM20-dependent DCM or heart failure).

ATRA may be administered by any suitable mode of administration. In certain embodiments, the ATRA is administered orally, intravenously, intra-arterially, or intracardially to a subject. In one embodiment, the ATRA is administered locally to the heart.

In certain embodiments, the method further comprises administering other agents for treating a cardiovascular disorder such as, but not limited to, an angiotensin-converting-enzyme (ACE) inhibitor, a beta blocker, or a diuretic.

Multiple cycles of treatment may be administered to a subject. In certain embodiments, the ATRA is administered according to a daily dosing regimen or intermittently.

In another aspect, the invention includes a method of increasing expression of RBM20 in a subject, the method comprising administering an effective amount of all-trans retinoic acid (ATRA) to the subject. In one embodiment, the subject has RBM20-dependent dilated cardiomyopathy.

In another aspect, the invention includes a method for detecting a genetic predisposition to developing RBM20-dependent dilated cardiomyopathy (DCM) and treating a subject for RBM20-dependent DCM, the method comprising: a) detecting whether the subject has a P633L mutation in RBM20, wherein the presence of the P633L mutation indicates that the subject has the genetic predisposition to developing RBM20-dependent DCM; and b) treating the subject for RBM20-dependent DCM if the subject is determined to have the genetic predisposition to developing RBM20-dependent DCM.

In certain embodiments, the subject is heterozygous or homozygous for the P633L mutation in the RBM20.

In certain embodiments, the treatment comprises administering a therapeutically effective amount of all-trans retinoic acid (ATRA) to the subject.

In certain embodiments, the treatment comprises administering an angiotensin-converting-enzyme (ACE) inhibitor, a beta blocker, or a diuretic to the subject.

In certain embodiments, the treatment comprises implanting an artificial pacemaker or cardioverter-defibrillator in the subject.

The P633L mutation can be detected by any suitable method such as, but not limited to, dynamic allele-specific hybridization (DASH), microarray analysis, Tetra-primer ARMS-PCR, a TaqMan 5'-nuclease assay; an Invader assay with Flap endonuclease (FEN), a Serial Invasive Signal Amplification Reaction (SISAR), an oligonucleotide ligase assay, restriction fragment length polymorphism (RFLP), single-strand conformation polymorphism, temperature gradient gel electrophoresis (TGGE), denaturing high performance liquid chromatography (DHPLC), sequencing, and immunoassay. In certain embodiments, the P633L mutation is detected using an allele-specific probe that selectively hybridizes to a nucleic acid comprising an RBM20 gene sequence encoding the P633L mutation, or a complement thereof. In other embodiments, the P633L mutation is detected using a set of allele-specific primers capable of selectively amplifying a nucleic acid comprising an RBM20 gene sequence encoding the P633L mutation, or a complement thereof.

In another aspect, the invention includes a kit for determining if a subject has a genetic predisposition to developing RBM20-dependent dilated cardiomyopathy (DCM) based on the detection of a P633L mutation in RMB20 in the subject's genome, said kit comprising (i) at least one allele-specific primer or allele-specific probe that selectively hybridizes to a nucleic acid comprising an RBM20 gene sequence encoding the P633L mutation, or a complement thereof.

In certain embodiments, the kit comprises an allele-specific probe that selectively hybridizes to a nucleic acid comprising an RBM20 gene sequence encoding the P633L mutation, or a complement thereof.

In certain embodiments, the kit comprises a set of allele-specific primers capable of selectively amplifying a nucleic acid comprising an RBM20 gene sequence encoding the P633L mutation, or a complement thereof.

In certain embodiments, the kit further comprises reagents for performing dynamic allele-specific hybridization (DASH), Tetra-primer ARMS-PCR, a TaqMan 5-nuclease assay; an Invader assay with Flap endonuclease (FEN), a Serial Invasive Signal Amplification Reaction (SISAR), an oligonucleotide ligase assay, restriction fragment length polymorphism (RFLP), single-strand conformation polymorphism, temperature gradient gel electrophoresis (TGGE), denaturing high performance liquid chromatography (DHPLC), sequencing, or an immunoassay. For example, the kit may comprise reagents for performing targeted sequencing of an amplified or captured nucleic acid comprising an RBM20 gene sequence. Both RBM20 alleles may be sequenced to determine if a P633L mutation is present at a single allele or both alleles.

In certain embodiments, the kit further comprises information, in electronic or paper form, comprising instructions on how to detect the P633L mutation and determine if the subject has a genetic predisposition to developing RBM20-dependent DCM.

In another aspect, the invention includes an induced pluripotent stem cell (IPSC) comprising at least one RBM20 allele encoding a P633L mutation. The IPSC can be heterozygous or homozygous for the RBM20 allele encoding the P633L mutation. In certain embodiments, the IPSC is derived from a human patient who has RBM20-dependent DCM.

In another aspect, the invention includes an iPSC-derived cardiomyocyte (IPSC-CM) produced by differentiation of an IPSC comprising at least one RBM20 allele encoding a P633L mutation, as described herein.

In another aspect, the invention includes a method of screening a candidate agent for treating dilated cardiomyopathy, the method comprising: a) contacting an IPSC-CM described herein with the candidate agent; and b) detecting one or more disease-relevant phenotypic effects of the candidate agent on the IPSC-CM. For example, the method can be used to screen one or more disease-relevant phenotypic effects such as, but not limited to, levels of expression of RBM20, RBM20-mediated splicing defects, calcium transients, and contractile capacity of cardiomyocytes.

In certain embodiments, the method further comprises comparing the effects of the candidate agent to the effects of the candidate agent on a control IPSC-CM derived from a normal subject that does not have the P633L mutation.

In certain embodiments, the method comprises: a) detecting decreased inotropic activity compared to the control IPSC-CM; b) detecting decreased chronotropic activity compared to the control IPSC-CM; c) detecting decreased contractile force compared to the control IPSC-CM; d) detecting a gene expression profile that differs from a gene expression profile of the control IPSC-CM; e) detecting calcium transients that are smaller than calcium transients displayed by the control IPSC-CM; f) detecting a weaker ability to resist mechanical stimulation compared to the control IPSC-CM; g) detecting a higher frequency of punctate distribution of sarcomeric alpha-actin compared to the control IPSC-CM; and h) detecting increased sarcomeric disorganization in response to contractile stimulation compared to the control IPSC-CM.

These and other embodiments of the subject invention will readily occur to those of skill in the art in view of the disclosure herein.

BRIEF DESCRIPTION OF THE DRAWINGS

FIG. 1C shows an alignment of RBM20 from human (SEQ ID NO:8) and six other vertebrates (SEQ ID NO:6 and (SEQ ID NO:7). Residues conserved between human RBM20 and another six species are indicated by (•) and amino acid deletions by (−).

FIG. 5A shows the reference RBM20 cDNA sequence (ENSG00000203867, SEQ ID NO:9) with translation (SEQ ID NO:10) on top. FIG. 5B shows the sequence electropherogram for Clone 3 (SEQ ID NO:9), referred to as "WT" in the manuscript. Translation (SEQ ID NO:10) is shown on top. FIG. 5C shows a sequence electropherogram for Clone 3B (SEQ ID NO:11), referred to as "P633L" in the manuscript. Translation (SEQ ID NO:12) is shown on top. Affected nucleotides are highlighted in gray. FIG. 5D shows a sequence electropherogram for Clone 34 (SEQ ID NO:13), referred to as "R634Q" in the manuscript. Translation (SEQ ID NO:14) is shown on top. Affected nucleotides are highlighted in gray. FIG. 5E shows a sequence electropherogram for Clone 23 (SEQ ID NO:15), referred to as "S635FS" in the manuscript. Translation (SEQ ID NO:16) is shown on top (*=STOP codon). Affected nucleotides are highlighted in gray.

FIGS. 6A-6F shows a time-series-based analysis of calcium transients upon treatment with different doses of ATRA for WT (FIG. 6A), DCM-1 (FIG. 6B), DCM-2 (FIG. 6C), P633L (FIG. 6D), R634Q (FIG. 6E), and S635FS (FIG. 6F). Upstroke time is the calcium influx time (n=12-18 per dose per cell line). Different doses of ATRA are indicated in different colors. The cell line is indicated on top of each panel. FIGS. 6G-6L shows a time-series-based analysis of contractile profiles of RBM20 WT and mutant iPSC-CMs upon treatment with different doses of ATRA for WT (FIG. 6G), DCM-1 (FIG. 6H), DCM-2 (FIG. 6I), P633L (FIG. 6J), R634Q (FIG. 6K), and S635FS (FIG. 6L). The values of WT iPSC-CMs at baseline were normalized to 1 (n=12 per dose per cell line). Different doses of ATRA are indicated in different colors. The cell line is indicated on top of each panel.

FIGS. 7A and 7B show characterization of RBM20 scramble mutation. FIG. 7A shows a schematic representation of the wild-type RS domain (SEQ ID NO:17) and scramble-mutated RS domain (SEQ ID NO:18); FIG. 7B shows results of a Western blot using anti-RBM20 and anti-alpha-tubulin antibodies for heart tissues of WT (+/+), Het (+/−) and Hom (−/−) mice.

FIG. 8A shows results of a Western blot using capillary electrophoresis using anti-RBM20 and anti-Actin antibodies for heart and muscle tissues. FIG. 8B shows quantification of protein bands with normalization to the Actin levels for the heart tissue. In two out of three mice, ATRA treatment increases RBM20 protein level.

DETAILED DESCRIPTION OF THE INVENTION

Figure 1A:
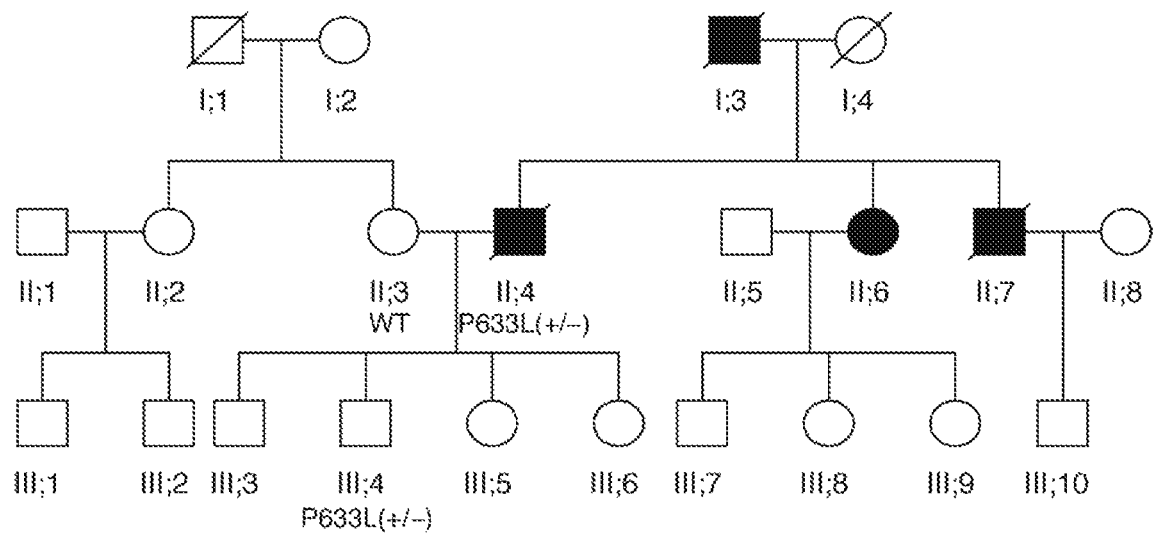
FIG. 1A shows a family pedigree of the proband. Square=male; circle=female; black=affected; white=unaffected; slash through the symbol=deceased; +=mutant allele; −=wild-type allele.

The practice of the present invention will employ, unless otherwise indicated, conventional methods of medicine, pharmacology, chemistry, and biochemistry, within the skill of the art. Such techniques are explained fully in the literature. See, e.g., R. O. Bonow, D. L. Mann, D. P. Zipes, P. Libby *Braunwald's Heart Disease: A Textbook of Cardiovascular Medicine* (Saunders; 9th edition, 2011); J. Watchie *Cardiovascular and Pulmonary Physical Therapy: A Clinical Manual* (Saunders, 2nd edition, 2009); R. A. Walsh *Molecular Mechanisms of Cardiac Hypertrophy and Failure* (CRC Press, 2004); *Genetics of Cardiovascular Disease*, Volume 124 (Progress in Molecular Biology and Translational Science, T. Chico ed., Academic Press, 2014); *Handbook of Experimental Immunology*, Vols. I-IV (D. M. Weir and C. C. Blackwell eds., Blackwell Scientific Publications); T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (3rd Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. Definitions

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a cell" includes a mixture of two or more cells, and the like.

The term "about," particularly in reference to a given quantity, is meant to encompass deviations of plus or minus five percent.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly, salts containing pharmaceutically acceptable cations include, but are not limited to, sodium, potassium, calcium, aluminum, lithium, and ammonium (including substituted ammonium).

An "effective amount" of ATRA is an amount sufficient to effect beneficial or desired results, such as an amount that increases expression of RBM20. An effective amount can be administered in one or more administrations, applications or dosages.

By "therapeutically effective dose or amount" of ATRA is intended an amount that, when administered as described herein, brings about a positive therapeutic response with respect to treatment of an individual for a heart condition associated with RBM20 deficiency (e.g., RBM20-dependent dilated cardiomyopathy or heart failure). By "positive therapeutic response" is intended that the individual undergoing treatment exhibits an improvement in one or more symptoms of the heart condition associated with RBM20 deficiency (e.g., RBM20-dependent dilated cardiomyopathy or heart failure), such as reduced RBM20-mediated splicing defects (e.g., reduced aberrant splicing of TTN transcripts), improved calcium handling (e.g., calcium transients with increased rate of calcium influx (i.e., reduction of calcium influx time)), and increased contractile capacity. Additionally, a therapeutically effective dose or amount may increase expression of RBM20. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a subject, particularly in a human, and includes: (a) increasing survival time; (b) decreasing the risk of death due to the disease; (c) preventing the disease from occurring in a subject which may be predisposed to the disease but has not yet been diagnosed as having it; (d) inhibiting the disease, i.e., arresting its development (e.g., reducing the rate of disease progression); and (e) relieving the disease, i.e., causing regression of the disease.

"Substantially purified" generally refers to isolation of a substance (e.g., compound, molecule, agent) such that the substance comprises the majority percent of the sample in which it resides. Typically in a sample, a substantially purified component comprises 50%, preferably 80%-85%, more preferably 90-95% of the sample.

The term "stem cell" refers to a cell that retains the ability to renew itself through mitotic cell division and that can differentiate into a diverse range of specialized cell types. Mammalian stem cells can be divided into three broad categories: embryonic stem cells, which are derived from blastocysts, adult stem cells, which are found in adult tissues, and cord blood stem cells, which are found in the umbilical cord. In a developing embryo, stem cells can differentiate into all of the specialized embryonic tissues. In adult organisms, stem cells and progenitor cells act as a repair system for the body by replenishing specialized cells. Totipotent stem cells are produced from the fusion of an egg and sperm cell. Cells produced by the first few divisions of the fertilized egg are also totipotent. These cells can differentiate into embryonic and extraembryonic cell types. Pluripotent stem cells are the descendants of totipotent cells and can differentiate into cells derived from any of the three germ layers. Multipotent stem cells can produce only cells of a closely related family of cells (e.g., hematopoietic stem cells differentiate into red blood cells, white blood cells, platelets, etc.). Unipotent cells can produce only one cell type, but have the property of self-renewal, which distinguishes them from non-stem cells. Induced pluripotent stem cells are a type of pluripotent stem cell derived from adult cells that have been reprogrammed into an embryonic-like pluripotent state. Induced pluripotent stem cells can be derived, for example, from adult somatic cells such as skin or blood cells.

As used herein, "reprogramming factors" refers to one or more, i.e. a cocktail, of biologically active factors that act on a cell to alter transcription, thereby reprogramming a cell to multipotency or to pluripotency. Reprogramming factors may be provided to the cells, e.g. cells from an individual with a family history or genetic make-up of interest for heart disease such as fibroblasts, adipocytes, etc.; individually or as a single composition, that is, as a premixed composition, of reprogramming factors. The factors may be provided at the same molar ratio or at different molar ratios. The factors may be provided once or multiple times in the course of culturing the cells of the subject invention. In some embodiments the reprogramming factor is a transcription factor, including without limitation, Oct3/4; Sox2; Klf4; c-Myc; Nanog; and Lin-28.

Somatic cells are contacted with reprogramming factors, as defined above, in a combination and quantity sufficient to reprogram the cell to pluripotency. Reprogramming factors may be provided to the somatic cells individually or as a single composition, that is, as a premixed composition, of reprogramming factors. In some embodiments the reprogramming factors are provided as a plurality of coding sequences on a vector.

By "isolated" is meant an indicated cell, population of cells, or molecule is separate and discrete from a whole organism or is present in the substantial absence of other cells or biological macromolecules of the same type.

The terms "subject," "individual" or "patient" are used interchangeably herein and refer to a vertebrate, preferably a mammal. By "vertebrate" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

As used herein, the term "probe" refers to a polynucleotide that contains a nucleic acid sequence complementary to a nucleic acid sequence present in the target nucleic acid analyte (e.g., at location of a mutation). The polynucleotide regions of probes may be composed of DNA, and/or RNA, and/or synthetic nucleotide analogs. Probes may be labeled in order to detect the target sequence. Such a label may be present at the 5' end, at the 3' end, at both the 5' and 3' ends, and/or internally.

An "allele-specific probe" hybridizes to only one of the possible alleles of a gene (e.g., hybridizes at the location of a mutation) under suitably stringent hybridization conditions.

The term "primer" as used herein, refers to an oligonucleotide that hybridizes to the template strand of a nucleic acid and initiates synthesis of a nucleic acid strand complementary to the template strand when placed under conditions in which synthesis of a primer extension product is induced, i.e., in the presence of nucleotides and a polymerization-inducing agent such as a DNA or RNA polymerase and at suitable temperature, pH, metal concentration, and salt concentration. The primer is preferably single-stranded for maximum efficiency in amplification, but may alternatively be double-stranded. If double-stranded, the primer can first be treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA or RNA synthesis. Typically, nucleic acids are amplified using at least one set of oligonucleotide primers comprising at least one forward primer and at least one reverse primer capable of hybridizing to regions of a nucleic acid flanking the portion of the nucleic acid to be amplified.

An "allele-specific primer" matches the sequence exactly of only one of the possible alleles of a gene (e.g., hybridizes at the location of a mutation), and amplifies only one specific allele if it is present in a nucleic acid amplification reaction.

As used herein, the terms "detection agent", "diagnostic agent", and "detectable label" refer to a molecule or substance capable of detection, including, but not limited to, fluorescers, chemiluminescers, chromophores, bioluminescent proteins, enzymes, enzyme substrates, enzyme cofactors, enzyme inhibitors, isotopic labels, semiconductor nanoparticles, dyes, metal ions, metal sols, ligands (e.g., biotin, streptavidin or haptens) and the like. The term "fluorescer" refers to a substance or a portion thereof which is capable of exhibiting fluorescence in the detectable range. Particular examples of labels which may be used in the practice of the invention include, but are not limited to, SYBR green, SYBR gold, a CAL Fluor dye such as CAL Fluor Gold 540, CAL Fluor Orange 560, CAL Fluor Red 590, CAL Fluor Red 610, and CAL Fluor Red 635, a Quasar dye such as Quasar 570, Quasar 670, and Quasar 705, an Alexa Fluor such as Alexa Fluor 350, Alexa Fluor 488, Alexa Fluor 546, Alexa Fluor 555, Alexa Fluor 594, Alexa Fluor 647, and Alexa Fluor 784, a cyanine dye such as Cy 3, Cy3.5, Cy5, Cy5.5, and Cy7, fluorescein, 2', 4', 5', 7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), rhodamine, carboxy-X-rhodamine (ROX), tetramethyl rhodamine (TAMRA), FITC, dansyl, umbelliferone, dimethyl acridinium ester (DMAE), Texas red, luminol, and quantum dots, enzymes such as alkaline phosphatase (AP), beta-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotransferase (HPH), thymidine kinase (TK), β-galactosidase (lacZ), and xanthine guanine phosphoribosyltransferase (XGPRT), beta-glucuronidase (gus), placental alkaline phosphatase (PLAP), and secreted embryonic alkaline phosphatase (SEAP). Enzyme tags are used with their cognate substrate. The terms also include chemiluminescent labels such as luminol, isoluminol, acridinium esters, and peroxyoxalate and bioluminescent proteins such as firefly luciferase, bacterial luciferase, Renilla luciferase, and aequorin. The terms also include isotopic labels, including radioactive and non-radioactive isotopes, such as, $^3$H, $^2$H, $^{120}$I, $^{123}$I, $^{124}$I, $^{125}$I, $^{131}$I, $^{35}$S, $^{11}$C, $^{13}$C, $^{14}$C, $^{32}$P, $^{15}$N, $^{13}$N, $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{154}$Gd, $^{155}$Gd, $^{156}$Gd, $^{157}$Gd, $^{158}$Gd, $^{15}$O, $^{186}$Re, $^{188}$Re, $^{51}$M, $^{52m}$Mn, $^{55}$Co, $^{72}$As, $^{75}$Br, $^{76}$Br, $^{82m}$Rb, and $^{83}$Sr. The terms also include color-coded microspheres of known fluorescent light intensities (see e.g., microspheres with xMAP technology produced by Luminex (Austin, TX); microspheres containing quantum dot nanocrystals, for example, containing different ratios and combinations of quantum dot colors (e.g., Qdot nanocrystals produced by Life Technologies (Carlsbad, CA); glass coated metal nanoparticles (see e.g., SERS nanotags produced by Nanoplex Technologies, Inc. (Mountain View, CA); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), glass microparticles with digital holographic code images (see e.g., CyVera microbeads produced by Illumina (San Diego, CA), near infrared (NIR) probes, and nanoshells. The terms also include contrast agents such as ultrasound contrast agents (e.g. SonoVue microbubbles comprising sulfur hexafluoride, Optison microbubbles comprising an albumin shell and octafluoropropane gas core, Levovist microbubbles comprising a lipid/galactose shell and an air core, Perflexane lipid microspheres comprising perfluorocarbon microbubbles, and Perflutren lipid microspheres comprising octafluoropropane encapsulated in an outer lipid shell), magnetic resonance imaging (MRI) contrast agents (e.g., gadodiamide, gadobenic acid, gadopentetic acid, gadoteridol, gadofosveset, gadoversetamide, gadoxetic acid), and radiocontrast agents, such as for computed tomography (CT), radiography, or fluoroscopy (e.g., diatrizoic acid, metrizoic acid, iodamide, iotalamic acid, ioxitalamic acid, ioglicic acid, acetrizoic acid, iocarmic acid, methiodal, diodone, metrizamide, iohexol, ioxaglic acid, iopamidol, iopromide, iotrolan, ioversol, iopentol, iodixanol, iomeprol, iobitridol, ioxilan, iodoxamic acid, iotroxic acid, ioglycamic acid, adipiodone, iobenzamic acid, iopanoic acid, iocetamic acid, sodium iopodate, tyropanoic acid, and calcium iopodate). As with many of the standard procedures associated with the practice of the invention, skilled artisans will be aware of additional labels that can be used.

The terms "candidate agent", "test agent", "agent", "substance" and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, CA), and MicroSource (New Milford, CT). Alternatively, libraries of natural compounds in the form of bacterial, fungal, plant and animal extracts are available from Pan Labs (Bothell, WA) or are readily producible.

Candidate agents may be small organic or inorganic compounds having a molecular weight of more than 50 and less than about 2,500 Da. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modeling.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery that all-trans retinoic acid (ATRA) can be used to upregulate expression of the splicing factor, RBM20, and revert the splicing, calcium handling, and contractility defects associated with RBM20-dependent DCM (see Examples). The inventors have shown that a P633L mutation in RBM20 is associated with a severe form of familial DCM. In addition, the inventors have developed a disease model of RBM20-dependent DCM using iPSC-derived cardiomyocytes (iPSC-CMs) comprising the P633L mutation. The RBM20 mutant iPSC-CMs exhibited splicing defects as well as impaired calcium handling and contractility. These mutant iPSC-CMs can be used as an in vitro disease model for disease-relevant screening to gain a better understanding of the disease mechanism and to test therapeutic approaches (see Example 1).

In order to further an understanding of the invention, a more detailed discussion is provided below regarding methods of treating RBM20-dependent DCM with ATRA, methods of genetic screening for the P633L mutation to identify patients with a genetic predisposition for developing RBM20-dependent DCM, as well as iPSC-CM based disease models of RBM20-dependent DCM and methods of using them in disease-relevant screening.

Upregulation of RBM20 for Treatment of Diseases Associated with RBM20-Deficiency In one aspect, the invention relates to the use of an agent that upregulates expression or activity of RBM20 for treatment of diseases associated with RBM20 deficiency such as RBM20-dependent DCM and heart failure. Any molecule (e.g., small molecule, transcription factor, protein, peptide, nucleic acid, oligonucleotide, or fragment thereof) that increases RBM20 activity and/or RBM20 expression may potentially be used. For example, all-trans retinoic acid (ATRA) upregulates RBM20 expression and is useful for treating RBM20-dependent DCM or heart failure. Without being bound by theory, mutations in the splicing factor RBM20 are associated with a severe form of familial DCM. In individuals heterozygous for a RBM20 mutant allele, increasing activity or expression of a functional RBM20 allele (and residual activity of a mutant allele, if any) can compensate for deficient RBM20 activity due to a defective allele and help to reduce splicing defects caused by a mutant RBM20 splicing factor (e.g., reduce aberrant splicing of transcripts such as TTN transcripts), improve calcium handling (i.e., reduction of calcium influx time), and increase contractile capacity of cardiomyocytes. In individuals homozygous for a RBM20 mutant allele having lower activity than the wild-type RBM20, increasing activity or expression of the mutant RBM20 allele may also help to compensate for deficient RBM20 activity.

Pharmaceutical Compositions

ATRA can be formulated into pharmaceutical compositions optionally comprising one or more pharmaceutically acceptable excipients. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition comprising ATRA can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the ATRA, or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (BASF, Mount Olive, New Jersey); sorbitan esters; lipids, such as phospholipids such as lecithin and other phosphatidylcholines, phosphatidylethanolamines (although preferably not in liposomal form; fatty acids and fatty esters; steroids, such as cholesterol; chelating agents, such as EDTA; and zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the ATRA (e.g., when contained in a drug delivery system) in the composition will vary depending on a number of factors, but will optimally be a therapeutically effective dose when the composition is in a unit dosage form or container (e.g., a vial). A therapeutically effective dose can be determined experimentally by repeated administration of increasing amounts of the composition in order to determine which amount produces a clinically desired endpoint.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, NJ (1998), and Kibbe, A. H., Handbook of Pharmaceutical Excipients, 3rd Edition, American Pharmaceutical Association, Washington, D.C., 2000.

The compositions encompass all types of formulations and in particular those that are suited for injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. Examples of suitable diluents for reconstituting solid compositions prior to injection include bacteriostatic water for injection, dextrose 5% in water, phosphate buffered saline, Ringer's solution, saline, sterile water, deionized water, and combinations thereof. With respect to liquid pharmaceutical compositions, solutions and suspensions are envisioned. Additional preferred compositions include those for oral, ocular, or localized delivery.

The pharmaceutical preparations herein can also be housed in a syringe, an implantation device, or the like, depending upon the intended mode of delivery and use. Preferably, the compositions comprising ATRA described herein are in unit dosage form, meaning an amount of a conjugate or composition of the invention appropriate for a single dose, in a premeasured or pre-packaged form.

The compositions herein may optionally include one or more additional agents, such as other drugs for treating RBM20-dependent DCM, heart failure, or other cardiovascular disorder, such as, but not limited to, vasodilators, such as epoprostenol (Flolan), iloprost (Ventavis), isosorbide dinitrate (Isordil), nesiritide (Natrecor), hydralazine (Apresoline), nitrates, and minoxidil, endothelin receptor antagonists, such as bosentan (Tracleer) and Ambrisentan (Letairis), drugs that open the blood vessels in the lungs to improve blood flow, such as sildenafil (Revatio, Viagra) and tadalafil (Cialis, Adcirca), calcium channel blockers, such as amlodipine (Norvasc, Lotrel), bepridil (Vascor), diltiazem (Cardizem, Tiazac), felodipine (Plendil), nifedipine (Adalat, Procardia), nimodipine (Nimotop), nisoldipine (Sular), and verapamil (Calan, Isoptin, Verelan), anticoagulants, such as warfarin (Coumadin, Jantoven), dalteparin (Fragmin), danaparoid (Orgaran), enoxaparin (Lovenox), heparin, and Tinzaparin (Innohep), angiotensin-converting enzyme (ACE) inhibitors, such as benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik), angiotensin II receptor blockers, such as candesartan (Atacand), eprosartan (Teveten), irbesartan (Avapro), losartan (Cozaar), telmisartan (Micardis), and valsartan (Diovan), beta blockers, such as acebutolol (Sectral), atenolol (Tenormin), betaxolol (Kerlone), bisoprolol/hydrochlorothiazide (Ziac), bisoprolol (Zebeta), carteolol (Cartrol), metoprolol (Lopressor, Toprol XL), nadolol (Corgard), propranolol (Inderal), sotalol (Betapace), timolol (Blocadren), diuretics, such as furosemide (Lasix), bumetanide (Bumex), torsemide (Demadex), hydrochlorothiazide (Esidrix), metolazone (Zaroxolyn), and spironolactone (Aldactone), antiplatelet agents, such as aspirin, ticlopidine, clopidogrel (Plavix), and dipyridamole, cholesterol-lowering drugs, such as statins, resins, nicotinic acid (niacin), gemfibrozil, and clofibrate, and digoxin, and bronchodilators, such as aminophylline, theophylline, salbutamol, salmeterol, bambuterol, clenbuterol, formoterol, indacaterol, tiotropium, and ipratropium bromide; and or other medications used to treat a subject for a condition or disease. Alternatively, such agents can be contained in a separate composition from the composition comprising ATRA and co-administered concurrently, before, or after the composition comprising the ATRA.

Administration

At least one therapeutically effective cycle of treatment with all-trans retinoic acid (ATRA) will be administered to a subject for treatment of a heart condition associated with RBM20 deficiency (e.g., RBM20-dependent dilated cardiomyopathy or heart failure). By "positive therapeutic response" is intended that the individual undergoing treatment exhibits an improvement in one or more symptoms of the heart condition associated with RBM20 deficiency (e.g., RBM20-dependent dilated cardiomyopathy or heart failure), such as reduced RBM20-mediated splicing defects (e.g., reduced aberrant splicing of TTN transcripts), improved calcium handling (e.g., calcium transients with increased rate of calcium influx (i.e., reduction of calcium influx time)), and increased contractile capacity of cardiomyocytes. Additionally, a therapeutically effective dose or amount may increase expression of RBM20.

In certain embodiments, multiple therapeutically effective doses of compositions comprising ATRA and/or one or more other therapeutic agents, such as other drugs for treating cardiomyopathy, heart failure or other cardiovascular disorder, such as, but not limited to, vasodilators, such as epoprostenol (Flolan), iloprost (Ventavis), isosorbide dinitrate (Isordil), nesiritide (Natrecor), hydralazine (Apresoline), nitrates, and minoxidil, endothelin receptor antagonists, such as bosentan (Tracleer) and Ambrisentan (Letairis), drugs that open the blood vessels in the lungs to improve blood flow, such as sildenafil (Revatio, Viagra) and tadalafil (Cialis, Adcirca), calcium channel blockers, such as amlodipine (Norvasc, Lotrel), bepridil (Vascor), diltiazem (Cardizem, Tiazac), felodipine (Plendil), nifedipine (Adalat, Procardia), nimodipine (Nimotop), nisoldipine (Sular), and verapamil (Calan, Isoptin, Verelan), anticoagulants, such as warfarin (Coumadin, Jantoven), dalteparin (Fragmin), danaparoid (Orgaran), enoxaparin (Lovenox), heparin, and Tinzaparin (Innohep), angiotensin-converting enzyme (ACE) inhibitors, such as benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik), angiotensin II receptor blockers, such as candesartan (Atacand), eprosartan (Teveten), irbesartan (Avapro), losartan (Cozaar), telmisartan (Micardis), and valsartan (Diovan), beta blockers, such as acebutolol (Sectral), atenolol (Tenormin), betaxolol (Kerlone), bisoprolol/hydrochlorothiazide (Ziac), bisoprolol (Zebeta), carteolol (Cartrol), metoprolol (Lopressor, Toprol XL), nadolol (Corgard), propranolol (Inderal), sotalol (Betapace), timolol (Blocadren), diuretics, such as furosemide (Lasix), bumetanide (Bumex), torsemide (Demadex), hydrochlorothiazide (Esidrix), metolazone (Zaroxolyn), and spironolactone (Aldactone), antiplatelet agents, such as aspirin, ticlopidine, clopidogrel (Plavix), and dipyridamole, cholesterol-lowering drugs, such as statins, resins, nicotinic acid (niacin), gemfibrozil, and clofibrate, and digoxin, and bronchodilators, such as aminophylline, theophylline, salbutamol, salmeterol, bambuterol, clenbuterol, formoterol, indacaterol, tiotropium, and ipratropium bromide; or other medications will be administered.

Compositions may be administered in accordance with any medically acceptable method known in the art. The compositions are typically, although not necessarily, administered orally, via injection (subcutaneously, intravenously, or intramuscularly), by infusion, or locally. Additional modes of administration are also contemplated, such as intra-arterial, intravascular, pulmonary, intracardiac, intramyocardial, intrapericardial, intraspinal, intralesion, intraparenchymatous, rectal, transdermal, transmucosal, intrathecal, intraocular, intraperitoneal, and so forth. In particular embodiments, compositions are administered into an artery, vein, or capillary of a subject.

The preparations according to the invention are also suitable for local treatment. In a particular embodiment, a composition of the invention is used for localized delivery of ATRA to the heart for the treatment of a heart condition associated with RBM20 deficiency (e.g., RBM20-dependent dilated cardiomyopathy or heart failure). For example, compositions comprising ATRA may be administered directly into the heart or vascular system (e.g., arteries, veins, or capillaries). The particular preparation and appropriate method of administration are chosen to target ATRA to a site where increased expression of RBM20 is needed to reduce splicing defects and improve cardiac function.

The pharmaceutical preparation can be in the form of a liquid solution or suspension immediately prior to administration, but may also take another form such as a syrup, cream, ointment, tablet, capsule, powder, gel, matrix, suppository, or the like. The pharmaceutical compositions comprising ATRA and other agents may be administered using the same or different routes of administration in accordance with any medically acceptable method known in the art.

In another embodiment of the invention, the pharmaceutical compositions comprising ATRA and/or other agents are in a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition.

The invention also provides a method for administering a conjugate comprising ATRA as provided herein to a patient suffering from a heart condition associated with RBM20 deficiency (e.g., RBM20-dependent dilated cardiomyopathy or heart failure) that is responsive to treatment with an ATRA contained in the conjugate or composition. The method comprises administering, via any of the herein described modes, a therapeutically effective amount of the conjugate or drug delivery system, preferably provided as part of a pharmaceutical composition. The method of administering may be used to treat any condition that is responsive to treatment with ATRA. More specifically, the compositions herein are effective for treating cardiomyopathy, particularly RBM20-dependent DCM and heart failure.

In another embodiment, the pharmaceutical compositions comprising ATRA and/or other agents are administered prophylactically, e.g., to prevent cardiovascular damage (e.g., prevent RBM20-mediated splicing defects, loss of contractile strength) or improve cardiac function. Such prophylactic uses will be of particular value for subjects with who have a genetic predisposition to developing RBM20-dependent DCM, such as those individuals with mutations in the RBM20 gene known to be linked to DCM.

Those of ordinary skill in the art will appreciate which conditions ATRA can effectively treat. The actual dose to be administered will vary depending upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case.

Purified ATRA (again, preferably provided as part of a pharmaceutical preparation) can be administered alone or in combination with one or more other therapeutic agents, such as other drugs for treating cardiomyopathy or a cardiovascular disorder, or other medications used to treat a particular condition or disease according to a variety of dosing schedules depending on the judgment of the clinician, needs of the patient, and so forth. The specific dosing schedule will be known by those of ordinary skill in the art or can be determined experimentally using routine methods. In certain embodiments, multiple therapeutically effective doses of the ATRA and/or other therapeutic agents will be administered according to a daily dosing regimen or intermittently. For example, a therapeutically effective dose can be administered, one day a week, two days a week, three days a week, four days a week, or five days a week, and so forth. By "intermittent" administration is intended the therapeutically effective dose can be administered, for example, every other day, every two days, every three days, and so forth. For example, in some embodiments, the ATRA will be administered twice-weekly or thrice-weekly for an extended period of time, such as for 1, 2, 3, 4, 5, 6, 7, 8 . . . 10 . . . 15 . . . 24 weeks, and so forth. By "twice-weekly" or "two times per week" is intended that two therapeutically effective doses of the agent in question is administered to the subject within a 7 day period, beginning on day 1 of the first week of administration, with a minimum of 72 hours, between doses and a maximum of 96 hours between doses. By "thrice weekly" or "three times per week" is intended that three therapeutically effective doses are administered to the subject within a 7 day period, allowing for a minimum of 48 hours between doses and a maximum of 72 hours between doses. For purposes of the present invention, this type of dosing is referred to as "intermittent" therapy. In accordance with the methods of the present invention, a subject can receive intermittent therapy (i.e., twice-weekly or thrice-weekly administration of a therapeutically effective dose) for one or more weekly cycles until the desired therapeutic response is achieved. Preferred compositions are those requiring dosing no more than once a day.

ATRA can be administered prior to, concurrent with, or subsequent to other agents. If provided at the same time as other agents, ATRA can be provided in the same or in a different composition. Thus, ATRA and other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising ATRA and a dose of a pharmaceutical composition comprising at least one other agent, such as another agent for treating DCM, hear failure or other cardiovascular disorder, which in combination comprise a therapeutically effective dose, according to a particular dosing regimen. Similarly, ATRA and one or more other therapeutic agents can be administered in at least one therapeutic dose. Administration of the separate pharmaceutical compositions can be performed simultaneously or at different times (i.e., sequentially, in either order, on the same day, or on different days), as long as the therapeutic effect of the combination of these substances is caused in the subject undergoing therapy.

Kits

The invention also provides kits comprising one or more containers holding compositions comprising ATRA and optionally one or more other agents for treating a heart condition associated with RBM20 deficiency (e.g., RBM20-dependent dilated cardiomyopathy or heart failure) or other cardiovascular disorder. Compositions can be in liquid form or can be lyophilized. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery devices. The delivery device may be pre-filled with the compositions.

The kit can also comprise a package insert containing written instructions for methods of using the compositions comprising ATRA for treating a subject for RBM20-dependent DCM. The package insert can be an unapproved draft package insert or can be a package insert approved by the Food and Drug Administration (FDA) or other regulatory body.

Methods for Detecting a Genetic Predisposition to RBM20-Dependent DCM

Methods for determining whether or not a subject has a genetic predisposition for developing RBM20-dependent DCM are provided herein. The methods are also useful for evaluating the risk of developing RBM20-dependent DCM, confirming a diagnosis of RBM20-dependent DCM, and for determining an appropriate treatment regimen for a subject. In some embodiments, the method includes detecting the presence of a genotype, for example, determining whether one or both alleles of the RBM20 gene in the subject encode a RBM20 splicing factor having the P633L mutation.

For genetic testing, a biological sample containing nucleic acids is collected from an individual. The biological sample is typically saliva or cells from buccal swabbing, but can be any sample from bodily fluids, tissue or cells that contains genomic DNA or RNA of the individual. In certain embodiments, nucleic acids from the biological sample are isolated, purified, and/or amplified prior to analysis using methods well-known in the art. See, e.g., Green and Sambrook *Molecular Cloning: A Laboratory Manual*(Cold Spring Harbor Laboratory Press; 4$^{th}$ edition, 2012); and *Current Protocols in Molecular Biology* (Ausubel ed., John Wiley & Sons, 1995); herein incorporated by reference in their entireties.

Mutations in the RBM20 gene can be detected in a sample by any suitable method known in the art. Detection of a mutation can be direct or indirect. For example, the mutated gene itself can be detected directly. Alternatively, the mutation can be detected indirectly from cDNAs, amplified RNAs or DNAs, or proteins expressed by the mutated RBM20 allele. Any method that detects a base change in a nucleic acid sample or an amino acid substitution in a protein can be used. For example, allele-specific probes that specifically hybridize to a nucleic acid containing the mutated sequence can be used to detect the mutation. A variety of nucleic acid hybridization formats are known to those skilled in the art. For example, common formats include sandwich assays and competition or displacement assays. Hybridization techniques are generally described in Hames, and Higgins "Nucleic Acid Hybridization, A Practical Approach," IRL Press (1985); Gall and Pardue, Proc. Natl. Acad. Sci. U.S.A., 63:378-383 (1969); and John et al Nature, 223:582-587 (1969).

Sandwich assays are commercially useful hybridization assays for detecting or isolating nucleic acids. Such assays utilize a "capture" nucleic acid covalently immobilized to a solid support and a labeled "signal" nucleic acid in solution. The clinical sample will provide the target nucleic acid. The "capture" nucleic acid and "signal" nucleic acid probe hybridize with the target nucleic acid to form a "sandwich" hybridization complex.

In one embodiment, the allele-specific probe is a molecular beacon. Molecular beacons are hairpin shaped oligonucleotides with an internally quenched fluorophore. Molecular beacons typically comprise four parts: a loop of about 18-30 nucleotides, which is complementary to the target nucleic acid sequence; a stem formed by two oligonucleotide regions that are complementary to each other, each about 5 to 7 nucleotide residues in length, on either side of the loop; a fluorophore covalently attached to the 5' end of the molecular beacon, and a quencher covalently attached to the 3' end of the molecular beacon. When the beacon is in its closed hairpin conformation, the quencher resides in proximity to the fluorophore, which results in quenching of the fluorescent emission from the fluorophore. In the presence of a target nucleic acid having a region that is complementary to the strand in the molecular beacon loop, hybridization occurs resulting in the formation of a duplex between the target nucleic acid and the molecular beacon. Hybridization disrupts intramolecular interactions in the stem of the molecular beacon and causes the fluorophore and the quencher of the molecular beacon to separate resulting in a fluorescent signal from the fluorophore that indicates the presence of the target nucleic acid sequence.

For detection, the molecular beacon is designed to only emit fluorescence when bound to a specific allele of the RBM20 gene. When the molecular beacon probe encounters a target sequence with as little as one non-complementary nucleotide, the molecular beacon preferentially stay in its natural hairpin state and no fluorescence is observed because the fluorophore remains quenched. See, e.g., Nguyen et al. (2011) Chemistry 17(46):13052-13058; Sato et al. (2011) Chemistry 17(41):11650-11656; Li et al. (2011) Biosens Bioelectron. 26(5):2317-2322; Guo et al. (2012) Anal. Bioanal. Chem. 402(10):3115-3125; Wang et al. (2009) Angew. Chem. Int. Ed. Engl. 48(5):856-870; and Li et al. (2008) Biochem. Biophys. Res. Commun. 373(4):457-461; herein incorporated by reference in their entireties.

In another embodiment, detection of the mutated sequence is performed using allele-specific amplification. In the case of PCR, amplification primers can be designed to bind to a portion of one of the disclosed genes, and the terminal base at the 3' end is used to discriminate between the major and minor alleles or mutant and wild-type forms of the genes. If the terminal base matches the major or minor allele, polymerase-dependent three prime extension can proceed. Amplification products can be detected with specific probes. This method for detecting point mutations or polymorphisms is described in detail by Sommer et al. in Mayo Clin. Proc. 64:1361-1372 (1989).

Tetra-primer ARMS-PCR uses two pairs of primers that can amplify two alleles of a gene in one PCR reaction. Allele-specific primers are used that hybridize at the location of the mutated sequence, but each matches perfectly to only one of the possible alleles. If a given allele is present in the PCR reaction, the primer pair specific to that allele will amplify that allele, but not the other allele of the gene. The two primer pairs for the different alleles may be designed such that their PCR products are of significantly different length, which allows them to be distinguished readily by gel electrophoresis. See, e.g., Munoz et al. (2009) J. Microbiol. Methods. 78(2):245-246 and Chiapparino et al. (2004) Genome. 47(2):414-420; herein incorporated by reference.

Mutations in the RBM20 gene may also be detected by ligase chain reaction (LCR) or ligase detection reaction (LDR). The specificity of the ligation reaction is used to discriminate between the major and minor alleles of the gene. Two probes are hybridized at the site of the mutation in a nucleic acid of interest, whereby ligation can only occur if the probes are identical to the target sequence. See e.g., Psifidi et al. (2011) PLoS One 6(1): e14560; Asari et al. (2010) Mol. Cell. Probes. 24(6):381-386; Lowe et al. (2010) Anal Chem. 82(13):5810-5814; herein incorporated by reference.

Mutations in the RBM20 gene can also be detected in a biological sample by sequencing and genotyping. In the former method, one simply carries out whole genome sequencing of a DNA sample, and uses the results to detect the present sequences. Whole genome analysis is used in the field of "personal genomics," and genetic testing services exist, which provide full genome sequencing using massively parallel sequencing. Massively parallel sequencing is described e.g. in U.S. Pat. No. 5,695,934, entitled "Massively parallel sequencing of sorted polynucleotides," and US 2010/0113283 A1, entitled "Massively multiplexed sequencing." Massively parallel sequencing typically involves obtaining DNA representing an entire genome, fragmenting it, and obtaining millions of random short sequences, which are assembled by mapping them to a reference genome sequence.

Commercial services are also available that are capable of genotyping approximately 1 million sequences for a fixed fee. Genetic analysis can be carried out with a variety of methods that do not involve massively parallel random sequencing. For example, a commercially available MassARRAY system can be used. This system uses matrix-assisted laser desorption ionization time-of-flight mass spectrometry (MALDI-TOF MS) coupled with single-base extension PCR for high-throughput multiplex detection of mutations. Another commercial system, the Illumina Golden Gate assay, generates mutation-specific PCR products that are subsequently hybridized to beads either on a solid matrix or in solution. Three oligonucleotides are synthesized for each mutant: two allele specific oligonucleotides (ASOs) that distinguish the mutated sequence, and a locus specific sequence (LSO) just downstream of the mutation site. The ASO and LSO sequences also contain target sequences for a set of universal primers, while each LSO also contains a particular address sequences (the "illumicode") complementary to sequences attached to beads.

As another example, an array comprising probes for detecting mutant alleles can be used. For example, SNP arrays are commercially available from Affymetrix and Illumina, which use multiple sets of short oligonucleotide probes for detecting known SNPs. The design of SNP arrays, such as manufactured by Affymetrix or Illumina, is described further in LaFamboise, "Single nucleotide polymorphism arrays: a decade of biological, computational and technological advances," Nuc. Acids Res. 37(13):4181-4193 (2009).

Another method that can be used for detection of mutant alleles is PCR-dynamic allele specific hybridization (DASH), which involves dynamic heating and coincident monitoring of DNA denaturation, as disclosed by Howell et al. (Nat. Biotech. 17:87-88, 1999). A target sequence is amplified (e.g., by PCR) using one biotinylated primer. The biotinylated product strand is bound to a streptavidin-coated microtiter plate well (or other suitable surface), and the non-biotinylated strand is rinsed away with alkali wash solution. An oligonucleotide probe, specific for one allele (e.g., the wild-type allele), is hybridized to the target at low temperature. This probe forms a duplex DNA region that interacts with a double strand-specific intercalating dye. When subsequently excited, the dye emits fluorescence proportional to the amount of double-stranded DNA (probe-target duplex) present. The sample is then steadily heated while fluorescence is continually monitored. A rapid fall in fluorescence indicates the denaturing temperature of the probe-target duplex. Using this technique, a single-base mismatch between the probe and target results in a significant lowering of melting temperature (Tm) that can be readily detected.

A variety of other techniques can be used to detect mutations, including but not limited to, the Invader assay with Flap endonuclease (FEN), the Serial Invasive Signal Amplification Reaction (SISAR), the oligonucleotide ligase assay, restriction fragment length polymorphism (RFLP), single-strand conformation polymorphism, temperature gradient gel electrophoresis (TGGE), and denaturing high performance liquid chromatography (DHPLC). See, for example Molecular *Analysis and Genome Discovery* (R. Rapley and S. Harbron eds., Wiley $1^{st}$ edition, 2004); Jones et al. (2009) New Phytol. 183(4):935-966; Kwok et al. (2003) Curr Issues Mol. Biol. 5(2):43-60; Munoz et al. (2009) J. Microbiol. Methods. 78(2):245-246; Chiapparino et al. (2004) Genome. 47(2):414-420; Olivier (2005) Mutat Res. 573(1-2):103-110; Hsu et al. (2001) Clin. Chem. 47(8): 1373-1377; Hall et al. (2000) Proc. Natl. Acad. Sci. U.S.A. 97(15):8272-8277; Li et al. (2011) J. Nanosci. Nanotechnol. 11(2):994-1003; Tang et al. (2009) Hum. Mutat. 30(10): 1460-1468; Chuang et al. (2008) Anticancer Res. 28(4A): 2001-2007; Chang et al. (2006) BMC Genomics 7:30; Galeano et al. (2009) BMC Genomics 10:629; Larsen et al. (2001) Pharmacogenomics 2(4):387-399; Yu et al. (2006) Curr. Protoc. Hum. Genet. Chapter 7: Unit 7.10; Lilleberg (2003) Curr. Opin. Drug Discov. Devel. 6(2):237-252; and U.S. Pat. Nos. 4,666,828; 4,801,531; 5,110,920; 5,268,267; 5,387,506; 5,691,153; 5,698,339; 5,736,330; 5,834,200; 5,922,542; and 5,998,137 for a description of such methods; herein incorporated by reference in their entireties.

If the mutation is located in the coding region of RBM20, the mutation can be identified indirectly by detection of the variant protein produced by the mutant allele. Variant proteins (i.e., containing an amino acid substitution encoded by the mutant allele) can be detected using antibodies specific for the variant protein. For example, immunoassays that can be used to detect variant proteins produced by mutant alleles include, but are not limited to, immunohistochemistry (IHC), western blotting, enzyme-linked immunosorbent assay (ELISA), radioimmunoassays (RIA), "sandwich" immunoassays, fluorescent immunoassays, and immunoprecipitation assays, the procedures of which are well known in the art (see, e.g., Schwarz et al. (2010) Clin. Chem. Lab. Med. 48(12):1745-1749; *The Immunoassay Handbook* (D. G. Wild ed., Elsevier Science; $3^{rd}$ edition, 2005); Ausubel et al, eds, 1994, *Current Protocols in Molecular Biology*, Vol. 1 (John Wiley & Sons, Inc., New York); Coligan *Current Protocols in Immunology* (1991); Harlow & Lane, *Antibodies: A Laboratory Manual* (1988); *Handbook of Experimental Immunology*, Vols. I-IV (D. M. Weir and C. C. Blackwell eds., Blackwell Scientific Publications); herein incorporated by reference herein in their entireties).

In certain embodiments, a probe set is used for determining if a subject has a genetic predisposition for developing RBM20-dependent DCM, wherein the probe set comprises a plurality of allele-specific probes for detecting mutations in RBM20 including at least one probe for detecting whether a P633L mutation in RBM20 is present in the subject's genome. In certain embodiments, the probe set further comprises one or more probes for detecting one or more additional mutations in RBM20. Exemplary mutations known to be associated with RBM20-dependent DCM include mutations within the arginine/serine-rich domain of RBM20, including amino acid changes in RBM20 at positions 634, 635, 636, 637, and 638, such as R634Q, R634W, S635A, R636S, R636H, R636C, S637G and P638L; mutations in the glutamate-rich region of RBM20, such as E913K; and the mutations, V535I, and R716Q. See, e.g., U.S. Pat. No. 8,563,705; Guo et al. (2012) Nat. Med. 18(5):766-773; Beqqali et al. (2016) Cardiovasc Res. 112 (1):452-463; Wyles et al. (2016) Hum Mol Genet. 25(2): 254-265; Streckfuss-Bömeke et al. (2017) J. Mol. Cell. Cardiol. 113:9-21; and Li et al. (2010) Clin Transl Sci. 3(3):90-97; herein incorporated by reference.

The probe set may comprise one or more allele-specific polynucleotide probes. An allele-specific probe hybridizes to only one of the possible alleles of the RBM20 gene under suitably stringent hybridization conditions. Individual polynucleotide probes comprise a nucleotide sequence derived from the nucleotide sequence of the target mutated RBM20 allele sequences or complementary sequences thereof. The nucleotide sequence of the polynucleotide probe is designed such that it corresponds to, or is complementary to the target mutated RBM20 allele sequences. The allele-specific polynucleotide probe can specifically hybridize under either stringent or lowered stringency hybridization conditions to a region of the target mutated RBM20 allele sequences, to the complement thereof, or to a nucleic acid sequence (such as a cDNA) derived therefrom.

The selection of the allele-specific polynucleotide probe sequences and determination of their uniqueness may be carried out in silico using techniques known in the art, for example, based on a BLASTN search of the polynucleotide sequence in question against gene sequence databases, such as the Human Genome Sequence, UniGene, dbEST or the non-redundant database at NCBI. In one embodiment of the invention, the allele-specific polynucleotide probe is complementary to the region of a single mutated RBM20 allele target DNA or mRNA sequence. Computer programs can also be employed to select allele-specific probe sequences that may not cross hybridize or may not hybridize non-specifically.

The allele-specific polynucleotide probes of the present invention may range in length from about 15 nucleotides to the full length of the coding target or non-coding target. In one embodiment of the invention, the polynucleotide probes are at least about 15 nucleotides in length. In another embodiment, the polynucleotide probes are at least about 20 nucleotides in length. In a further embodiment, the polynucleotide probes are at least about 25 nucleotides in length. In another embodiment, the polynucleotide probes are between about 15 nucleotides and about 500 nucleotides in length. In other embodiments, the polynucleotide probes are between about 15 nucleotides and about 450 nucleotides, about 15 nucleotides and about 400 nucleotides, about 15 nucleotides and about 350 nucleotides, about 15 nucleotides and about 300 nucleotides, about 15 nucleotides and about 250 nucleotides, about 15 nucleotides and about 200 nucleotides in length. In some embodiments, the probes are at least 15 nucleotides in length. In some embodiments, the probes are at least 15 nucleotides in length. In some embodiments, the probes are at least 20 nucleotides, at least 25 nucleotides, at least 50 nucleotides, at least 75 nucleotides, at least 100 nucleotides, at least 125 nucleotides, at least 150 nucleotides, at least 200 nucleotides, at least 225 nucleotides, at least 250 nucleotides, at least 275 nucleotides, at least 300 nucleotides, at least 325 nucleotides, at least 350 nucleotides, at least 375 nucleotides in length.

The allele-specific polynucleotide probes of a probe set can comprise RNA, DNA, RNA or DNA mimetics, or combinations thereof, and can be single-stranded or double-stranded. Thus, the polynucleotide probes can be composed of naturally-occurring nucleobases, sugars and covalent internucleoside (backbone) linkages as well as polynucleotide probes having non-naturally-occurring portions which function similarly. Such modified or substituted polynucleotide probes may provide desirable properties such as, for example, enhanced affinity for a target gene and increased stability. The probe set may comprise a coding target and/or a non-coding target. Preferably, the probe set comprises a combination of a coding target and non-coding target.

In another embodiment, the invention provides a set of allele-specific primers for determining if a subject has a genetic predisposition for developing RBM20-dependent DCM, wherein the set of allele-specific primers comprises a plurality of allele-specific primers for detecting mutations in RBM20 including at least one allele-specific primer for detecting whether a P633L mutation in RBM20 is present in at least one allele of an RMB20 gene in the subject's genome. An allele-specific primer matches the sequence exactly of only one of the possible mutated RBM20 alleles, hybridizes at the location of the RBM20 mutation, and amplifies only one specific mutated RBM20 allele if it is present in a nucleic acid amplification reaction. For use in amplification reactions such as PCR, a pair of primers can be used for detection of a mutated RBM20 allele sequence. Each primer is designed to hybridize selectively to a single allele at the site of the mutation in the RBM20 gene under stringent conditions, particularly under conditions of high stringency, as known in the art. The pairs of allele-specific primers are usually chosen so as to generate an amplification product of at least about 50 nucleotides, more usually at least about 100 nucleotides. Algorithms for the selection of primer sequences are generally known, and are available in commercial software packages. These primers may be used in standard quantitative or qualitative PCR-based assays for SNP genotyping of subjects. Alternatively, these primers may be used in combination with probes, such as molecular beacons in amplifications using real-time PCR.

A label can optionally be attached to or incorporated into an allele-specific probe or primer polynucleotide to allow detection and/or quantitation of a target mutated RBM20 allele sequence. The target mutated RBM20 polynucleotide may be from genomic DNA, expressed RNA, a cDNA copy thereof, or an amplification product derived therefrom, and may be the positive or negative strand, so long as it can be specifically detected in the assay being used. Similarly, an antibody may be labeled that detects a polypeptide expression product of the mutated RBM20 allele.

In certain multiplex formats, labels used for detecting different mutant RBM20 alleles may be distinguishable. The label can be attached directly (e.g., via covalent linkage) or indirectly, e.g., via a bridging molecule or series of molecules (e.g., a molecule or complex that can bind to an assay component, or via members of a binding pair that can be incorporated into assay components, e.g. biotin-avidin or streptavidin). Many labels are commercially available in activated forms which can readily be used for such conjugation (for example through amine acylation), or labels may be attached through known or determinable conjugation schemes, many of which are known in the art.

Detectable labels useful in the practice of the invention may include any molecule or substance capable of detection, including, but not limited to, fluorescers, chemiluminescers, chromophores, bioluminescent proteins, enzymes, enzyme substrates, enzyme cofactors, enzyme inhibitors, isotopic labels, semiconductor nanoparticles, dyes, metal ions, metal sols, ligands (e.g., biotin, streptavidin or haptens) and the like. The term "fluorescer" refers to a substance or a portion thereof which is capable of exhibiting fluorescence in the detectable range. Particular examples of labels which may be used in the practice of the invention include, but are not limited to, SYBR green, SYBR gold, a CAL Fluor dye such as CAL Fluor Gold 540, CAL Fluor Orange 560, CAL Fluor Red 590, CAL Fluor Red 610, and CAL Fluor Red 635, a Quasar dye such as Quasar 570, Quasar 670, and Quasar 705, an Alexa Fluor such as Alexa Fluor 350, Alexa Fluor 488, Alexa Fluor 546, Alexa Fluor 555, Alexa Fluor 594, Alexa Fluor 647, and Alexa Fluor 784, a cyanine dye such as Cy 3, Cy3.5, Cy5, Cy5.5, and Cy7, fluorescein, 2', 4', 5', 7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), rhodamine, carboxy-X-rhodamine (ROX), tetramethyl rhodamine (TAMRA), FITC, dansyl, umbelliferone, dimethyl acridinium ester (DMAE), Texas red, luminol, and quantum dots, enzymes such as alkaline phosphatase (AP), beta-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotransferase (HPH), thymidine kinase (TK), β-galactosidase (lacZ), and xanthine guanine phosphoribosyltransferase (XGPRT), beta-glucuronidase (gus), placental alkaline phosphatase (PLAP), and secreted embryonic alkaline phosphatase (SEAP). Enzyme tags are used with their cognate substrate. The terms also include chemiluminescent labels such as luminol, isoluminol, acridinium esters, and peroxyoxalate and bioluminescent proteins such as firefly luciferase, bacterial luciferase, Renilla luciferase, and aequorin. The terms also include isotopic labels, including radioactive and non-radioactive isotopes, such as, $^3$H, $^2$H, $^{120}$I, $^{123}$I, $^{124}$I, $^{125}$I, $^{131}$I, $^{35}$S, $^{11}$C, $^{13}$C, $^{14}$C, $^{32}$P, $^{15}$N, $^{13}$N, $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{154}$Gd, $^{155}$Gd, $^{156}$Gd, $^{157}$Gd, $^{158}$Gd, $^{15}$O, $^{186}$Re, $^{188}$Re, $^{51}$M, $^{52m}$Mn, $^{55}$Co, $^{72}$As, $^{75}$Br, $^{76}$Br, $^{82m}$Rb, and $^{83}$Sr. The terms also include color-coded microspheres of known fluorescent light intensities (see e.g., microspheres with xMAP technology produced by Luminex (Austin, TX); microspheres containing quantum dot nanocrystals, for example, containing different ratios and combinations of quantum dot colors (e.g., Qdot nanocrystals produced by Life Technologies (Carlsbad, CA); glass coated metal nanoparticles (see e.g., SERS nanotags produced by Nanoplex Technologies, Inc. (Mountain View, CA); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), glass microparticles with digital holographic code images (see e.g., CyVera microbeads produced by Illumina (San Diego, CA), near infrared (NIR) probes, and nanoshells. The terms also include contrast agents such as ultrasound contrast agents (e.g. SonoVue microbubbles comprising sulfur hexafluoride, Optison microbubbles comprising an albumin shell and octafluoropropane gas core, Levovist microbubbles comprising a lipid/galactose shell and an air core, Perflexane lipid microspheres comprising perfluorocarbon microbubbles, and Perflutren lipid microspheres comprising octafluoropropane encapsulated in an outer lipid shell), magnetic resonance imaging (MRI) contrast agents (e.g., gadodiamide, gadobenic acid, gadopentetic acid, gadoteridol, gadofosveset, gadoversetamide, gadoxetic acid), and radiocontrast agents, such as for computed tomography (CT), radiography, or fluoroscopy (e.g., diatrizoic acid, metrizoic acid, iodamide, iotalamic acid, ioxitalamic acid, ioglicic acid, acetrizoic acid, iocarmic acid, methiodal, diodone, metrizamide, iohexol, ioxaglic acid, iopamidol, iopromide, iotrolan, ioversol, iopentol, iodixanol, iomeprol, iobitridol, ioxilan, iodoxamic acid, iotroxic acid, ioglycamic acid, adipiodone, iobenzamic acid, iopanoic acid, iocetamic acid, sodium iopodate, tyropanoic acid, and calcium iopodate). As with many of the standard procedures associated with the practice of the invention, skilled artisans will be aware of additional labels that can be used.

The methods are also of use for determining a therapeutic regimen or determining if a subject will benefit from treatment with a therapeutic regimen. For example, a subject identified as having a genetic predisposition for developing RBM20-dependent DCM (i.e., having one or more mutations in RBM20 known to be associated with DCM) may be treated with ATRA in advance of developing RBM20-dependent DCM to avoid heart damage that would be caused by aberrant splicing in the absence of treatment (i.e., to increase expression or activity of RBM20 to compensate for the presence of a mutant RBM20 allele having deficient activity). In addition, a subject already showing cardiovascular symptoms of disease may be administered, for example, an angiotensin-converting-enzyme (ACE) inhibitor, a beta blocker, or a diuretic, or other drug for treatment of DCM or a cardiovascular disorder. In certain embodiments, treatment of a subject already exhibiting heart damage may comprise implanting an artificial pacemaker or cardioverter-defibrillator in the subject.

Induced Pluripotent Stem Cell-Derived Cardiomyocytes as Disease Models of RBM20-Dependent DCM and their Use in Disease-Relevant Screening Induced pluripotent stem cell-derived cardiomyocytes (IPSC-CMs) comprising one or more DCM-like mutations (e.g., comprising at least one RBM20 allele encoding a P633L mutation) can be used to model RBM20-deficient DCM in vitro and in disease-relevant screening to assess the efficacy of new therapeutic approaches. In one embodiment, the IPSC-CMs comprise at least one RBM20 allele encoding a P633L mutation. The IPSC-CMs can be heterozygous or homozygous for the RBM20 allele encoding the P633L mutation. In certain embodiments, an induced pluripotent stem cell is derived from a human patient who has the P633L mutation associated with RBM20-dependent DCM. In other embodiments, the genome of an induced pluripotent stem cell is genetically modified to introduce the P633L mutation into one or more alleles of the RBM20 gene.

Methods for modifying the genome of cells are well known in the art. For example, the genome of IPSCs or IPSC-CMs can be modified to introduce one or more mutations known to be linked to DCM using engineered nucleases by nonhomologous end-joining (NHEJ) or homologous recombination (HR). For a review of various genome editing technologies, including the use of a clustered regularly interspaced short palindromic repeats (CRISPR)/Cas9 genome editing system, meganucleases, zinc finger nucleases (ZFNs), and transcription activator-like effector-based nucleases (TALEN). see, e.g., *Genome Editing and Engineering: From TALENs, ZFNs and CRISPRs to Molecular Surgery* (K. Appasani ed., Cambridge University Press, 2018), *CRISPR-Cas: A Laboratory Manual Lab Manual*(J. Doudna and P. Mali eds., Cold Spring Harbor Laboratory Press; Lab Manual, 2016), *Targeted Genome Editing Using Site-Specific Nucleases: ZFNs, TALENs, and the CRISPR/Cas9 System* (T. Yamamoto ed., Springer, 2015), Zhang et al. (2014) Hum. Mol. Genet. 23(R1): R40-46; Gori et al. (2015) Hum. Gene Ther. 26(7):443-451; Vasileva et al. (2015) Cell Death Dis. 6:e1831, Maeder et al. (2016) Mol Ther. 24(3): 430-446, Hotta et al. (2015) Annu Rev Genet. 49:47-70; herein incorporated by reference in their entireties.

Induced pluripotent stem cells can be differentiated into cardiomyocytes by methods well known in the art. For example, IPSCs can be differentiated into cardiomyocytes in culture by modulation of Wnt signaling. This method involves adding a GSK3B inhibitor to cultures to potentiate WNT signaling and induce differentiation of the IPSCs into cardiomyocytes. A WNT inhibitor is later added to attenuate WNT signaling. A chemically defined culture medium such as CDM3, consisting of RPMI 1640, rice-derived recombinant human albumin, and L-ascorbic acid 2-phosphate, can be used during differentiation as well as for maintenance of the induced cardiomyocytes. See, e.g., Burridge P W, Holmström A, Wu J C. Chemically Defined Culture and Cardiomyocyte Differentiation of Human Pluripotent Stem Cells. In: Current Protocols in Human Genetics. 2015. p. 21.3.1-21.3.15; herein incorporated by reference in its entirety.

IPSC-CMs comprising one or more DCM-linked mutations (e.g., at least one RBM20 allele encoding a P633L mutation) can be used in disease-relevant screening. For example, the cardiomyocytes can be exposed to one or more candidate agents. Candidate agents may include small molecules, macromolecules (e.g., proteins, peptides), drugs, genetic constructs, electrical changes, and the like. Screening may include testing a candidate agent such as a therapeutic drug at a range of dosages. The method can be used to screen for one or more disease-relevant phenotypic effects and may involve determining the effects of an agent on various morphologic, genetic, or functional parameters. For example, screening may involve monitoring calcium transient amplitudes, intracellular $Ca^{2+}$ levels, calcium influx time, contractile force, cardiomyocyte beating rate, sarcomeric α-actinin distribution, and gene expression profiling. In particular embodiments, such screening may be used to identify a therapeutic agent that can be used to increase expression or activity of RBM20, and/or reduce RBM20-mediated splicing defects, and/or reduce calcium influx time, and/or increase contractile capacity of cardiomyocytes.

For example, agents that modulate a phenotype may increase or decrease RBM20 expression by at least 10%, at least 20%, at least 30%, at least 40%, at least 50%, at least 60%, at least 70%, at least 80%, or at least 90%, or more, relative to a control that has not been exposed to the agent.

Agents that modulate RBM20 expression may be subjected to directed or random and/or directed chemical modifications, such as acylation, alkylation, esterification, amidification, etc. to produce structural analogs. Such structural analogs include those that increase bioavailability, and/or reduce cytotoxicity. Those skilled in the art can readily envision and generate a wide variety of structural analogs, and test them for desired properties such as increased bioavailability and/or reduced cytotoxicity, etc.

RBM20 expression can be measured using any suitable method for assaying RNA expression. The effect of a candidate agent may be determined by measuring RNA at several time points. For example, the production of RNA may be measured at 5 minutes, 30 minutes, 1 hour, 2 hours, 4 hours, 8 hours, 12 hours, 24 hours, 36 hours, 48 hours, 72 hours, 120 hours, 1 week, 2 weeks, or up to 1 month, after contacting a cell with a candidate agent.

After identifying an agent that increases RBM20 expression, the method may comprise testing the agent in vivo to determine whether it can decrease the severity of at least one symptom of DCM, or treat an animal for DCM. Any phenotype produced in the in vivo system may be monitored at different points before and after administering the candidate agent to the animal. For example, the effect of a candidate agent may be determined by measuring a phenotype at several time points. For example, the production of a phenotype may be measured at 0 hours, 12 hours, 24 hours, 36 hours, 48 hours, 72 hours, 120 hours, 1 week, 2 weeks, 1 month, 2 months, 3 months, 5 months, etc., after contacting the cell with a candidate agent.

In certain embodiments, cardiomyocytes are stimulated with a positive inotropic stress, such as a β-adrenergic agonist before, during or after contacting the cells with the candidate agent. In some embodiments the β-adrenergic agonist is norepinephrine. Cardiomyocytes with DCM-linked mutations may have an initially positive chronotropic effect in response to a positive inotropic stress, but later exhibit negative effects characteristic of heart failure such as having reduced beating rates, diminished contractile capacity, and an abnormal sarcomeric α-actinin distribution.

In certain embodiments, the screening of a candidate agent further comprises comparing the effects of the candidate agent on IPSC-CMs comprising one or more disease-linked mutations (e.g., a P633L mutation in RBM20) to the effects of the candidate agent on control IPSC-CMs derived from a normal healthy subject (i.e., not having any known DCM-linked mutations). For example, disease-relevant phenotypic effects may include, but are not limited to, decreased inotropic activity compared to the control IPSC-CMs; b) decreased chronotropic activity compared to the control IPSC-CMs; c) decreased contractile force compared to the control IPSC-CM; d) a gene expression profile that differs from a gene expression profile of the control IPSC-CMs; e) calcium transients that are smaller than calcium transients displayed by the control IPSC-CMs; f) weaker ability to resist mechanical stimulation compared to the control IPSC-CMs; g) a higher frequency of punctate distribution of sarcomeric alpha-actin compared to the control IPSC-CMs; and h) increased sarcomeric disorganization in response to contractile stimulation compared to the control IPSC-CMs.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

In Vitro Model of RBM20-Deficient DCM Identifies Retinoic Acid as a Therapeutic Candidate Introduction Mutations in the splicing factor RBM20 are associated with a severe form of familial DCM. We identified a new mutation in RBM20 that co-segregates with DCM in a family we investigated. To evaluate the pathogenic potential of this new variant in RBM20 we established an in vitro model of DCM using a combination of genome editing tools and a high-throughput method to quantify disease relevant phenotypes in iPSC-derived cardiomyocytes (iPSC-CMs). We further demonstrated the therapeutic potential of all-trans retinoic acid (ATRA) for patients with RBM20-deficient DCM.

Results

Identification of a New Mutation in RBM20

Figure 1B:
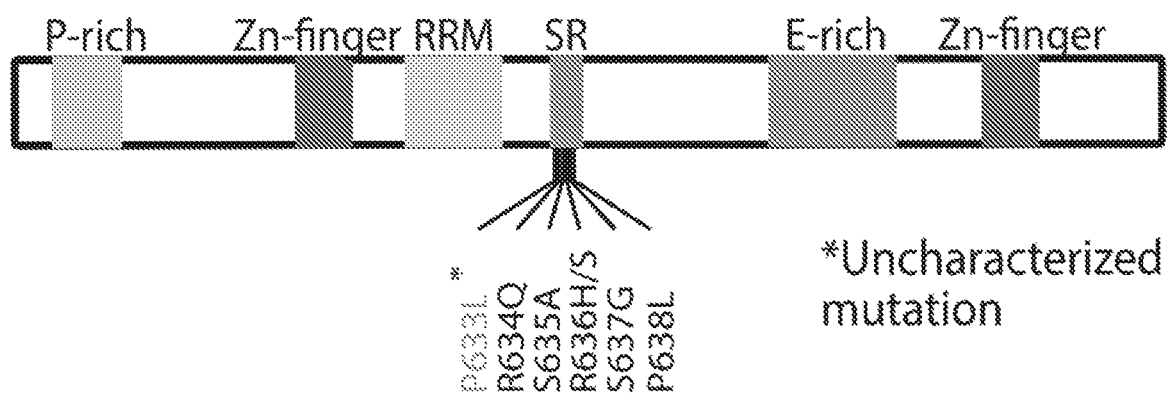
FIG. 1B shows a schematic representation of the RBM20 protein with predicted functional domains: P-rich is proline rich, Zn finger is Zinc finger domain, RRM is RNA-Recognition motif, and SR is serine/arginine-rich domain, and E-rich is glutamate rich. The residues that are altered by previously described RBM20 missense mutations (634, 636, 637, and 638) are indicated. The new identified mutation is highlighted in gray.
Figure 4:
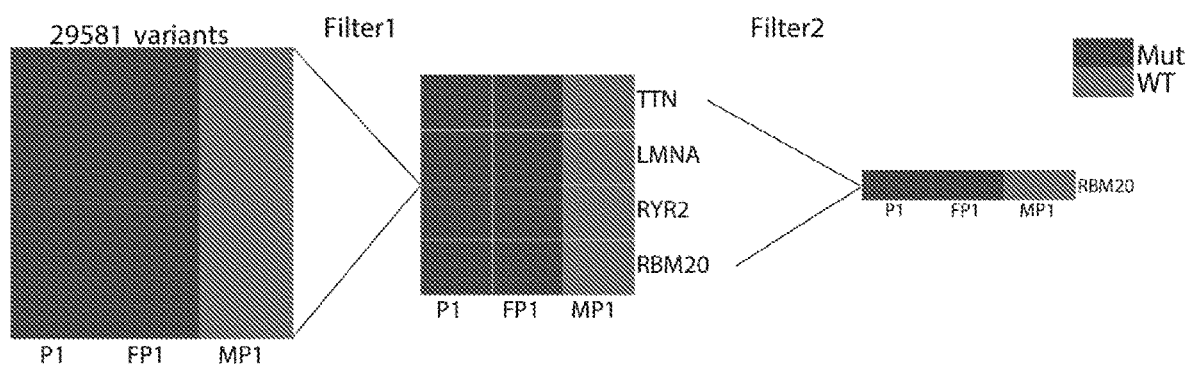
FIG. 4 shows a schematic of the workflow for the identification of disease-causing mutations in the proband family. 29581 variants in common between II;4 and III;4 and absent in II;3 were applied to Filter 1. Filter 1 includes previous database annotation, frequency<0.05 in ExAC and gene annotation. The 7 variants in 4 genes that passed the Filter 1 were manually evaluated (Filter 2).
Figure 5A:
FIGS. 5A-5E show sequence electropherograms showing the RBM20 mutation hotspot in the edited cell lines.
Figure 5B:
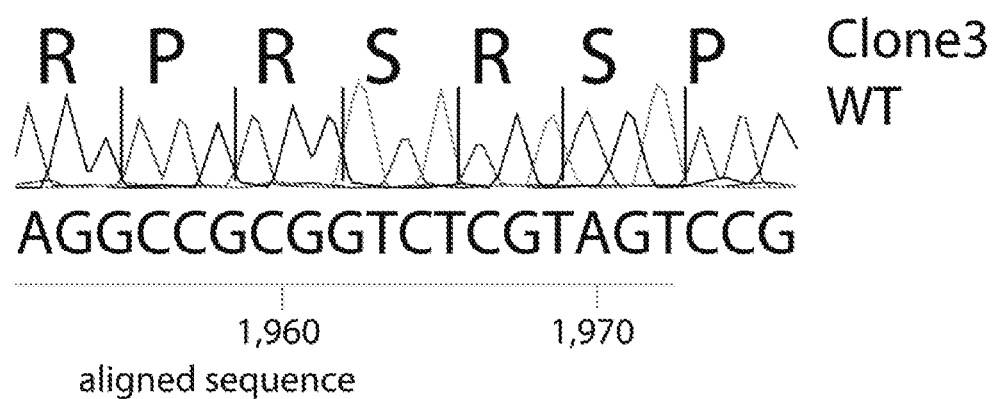
Figure 5C:
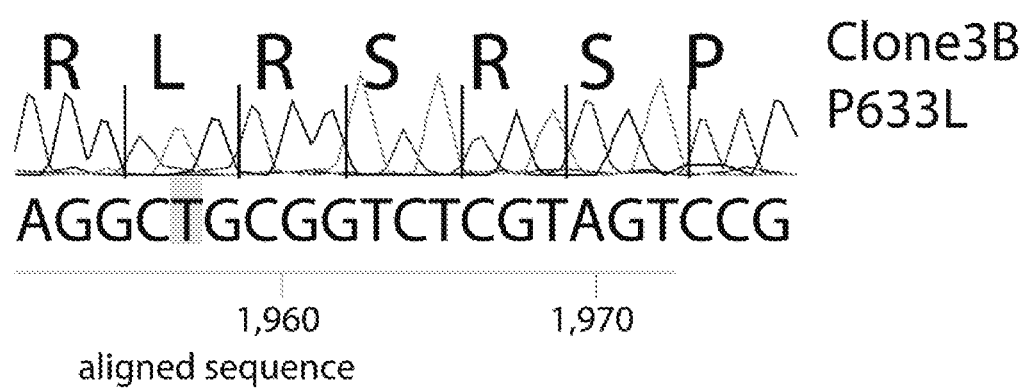
Figure 5D:
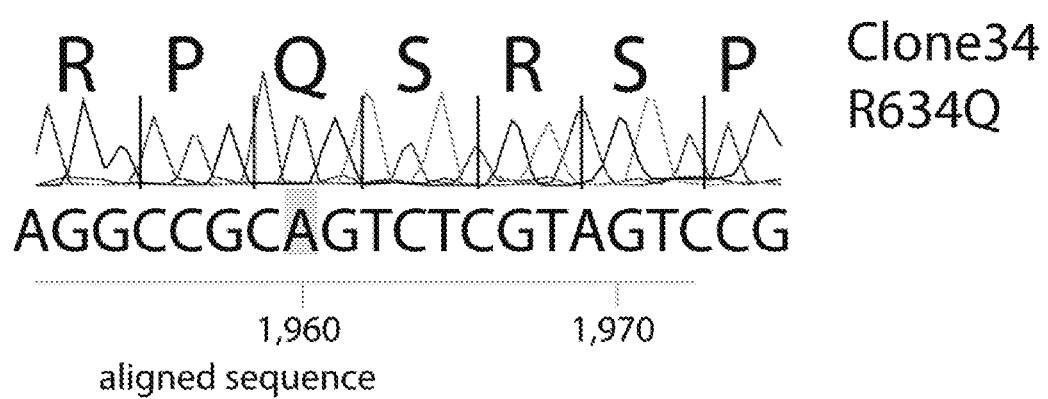
Figure 5E:
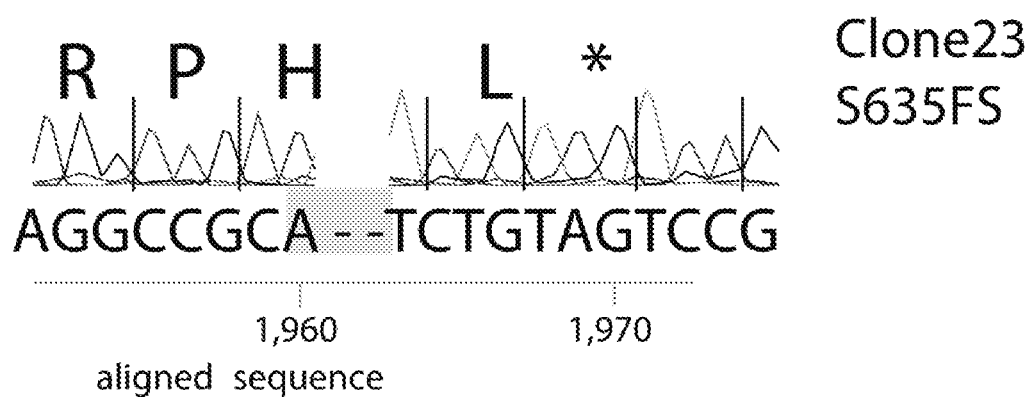

We identified a family with familial DCM (FIG. 1A), where the grandfather (I;3), father (II;4) and uncle (II;7) of the proband (Ill;4) passed away at ages 74, 69 and 53 respectively with a diagnosis of DCM. The proband presented with a mildly dilated left ventricle and a mildly reduced ejection fraction in 2002. To identify the disease-causing mutation in this family, we performed exome sequencing on the proband, his father (II;4), and his mother (II;3). The mother is unaffected by DCM. We found 29,581 variants present in both father and son, but not in the mother. As we didn't find any previously-reported DCM-causing mutation, we examined all variants in genes previously linked to DCM[12] (FIG. 4) Excluding variants occurring at frequency higher than 5% in ExAC left seven variants in four genes:

TTN, LMNA, RYR2 and RBM20. Independently, we performed panel sequencing on the later (II;4) targeting 95 prevalent sudden cardiac death related genes as previously described[13]. In both strategies, a missense mutation in RBM20 captured our interest because it is adjacent to a known mutation hotspot[14,15] in the highly evolutionarily conserved SR domain (FIG. 1B). The mutation is a proline to leucine change at amino acid position 633. All of the immediately following positions in RBM20 from 634 to 638 were previously associated with familial DCM.

Figure 1D:
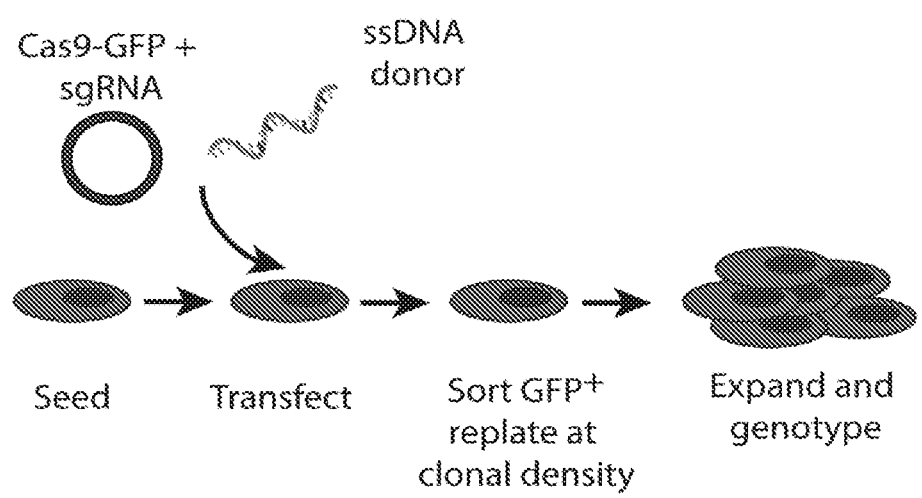
FIG. 1D shows a schematic of genome editing strategy. ssDNA is single stranded DNA, sgRNA is single guide RNA.
Figure 1E:
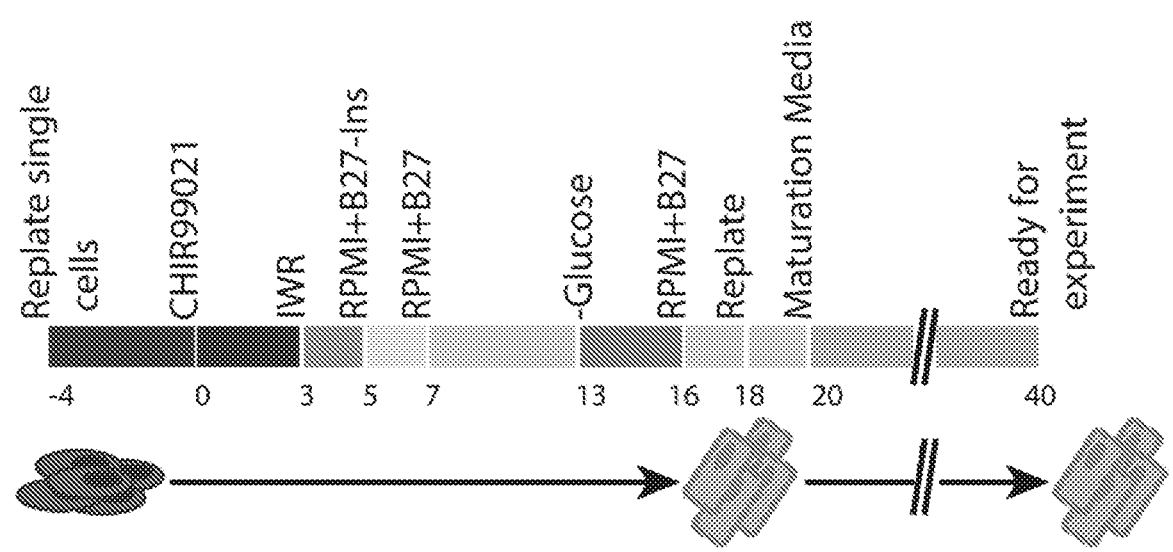
FIG. 1E shows a schematic of cardiomyocyte differentiation from iPSC annotated with the corresponding media supplementations. CHIR99021 is RPMI+B27-Ins+CHIR99021; IWR is RPMI+B27-Ins+IWR; −Glucose is RPMI −Glucose+B27-Ins.

Generation of Isogenic iPSC-CM Line to Study the Effect of P633L Mutation In Vitro To evaluate the pathogenic potential of the P633L mutation independently of the genomic background of the patient, we generated a set of isogenic iPSC lines using CRISPR-Cas9 (FIG. 1D). In an iPSC line derived from a healthy individual we introduced either the P633L mutation, or the R634Q mutation previously described as pathogenic[15], or a frameshift mutation at position 635 (S635FS) which results in the formation of a premature stop codon and consequent KO via the nonsense mediated decay pathway (FIG. 5)[16]. All editing events resulted in homozygous mutations. One clone that underwent the genome editing procedure without gaining a mutation in the RBM20 gene was also selected and used as healthy control. All the iPSC lines were differentiated into iPSC-CMs via modulation of WNT signaling as previously described[17] and selected via two rounds of glucose starvation and matured for 4 more weeks before the experiment (FIG. 1E).

Splicing Deregulation in RBM20 Mutant Cardiomyocytes

Figure 2A:
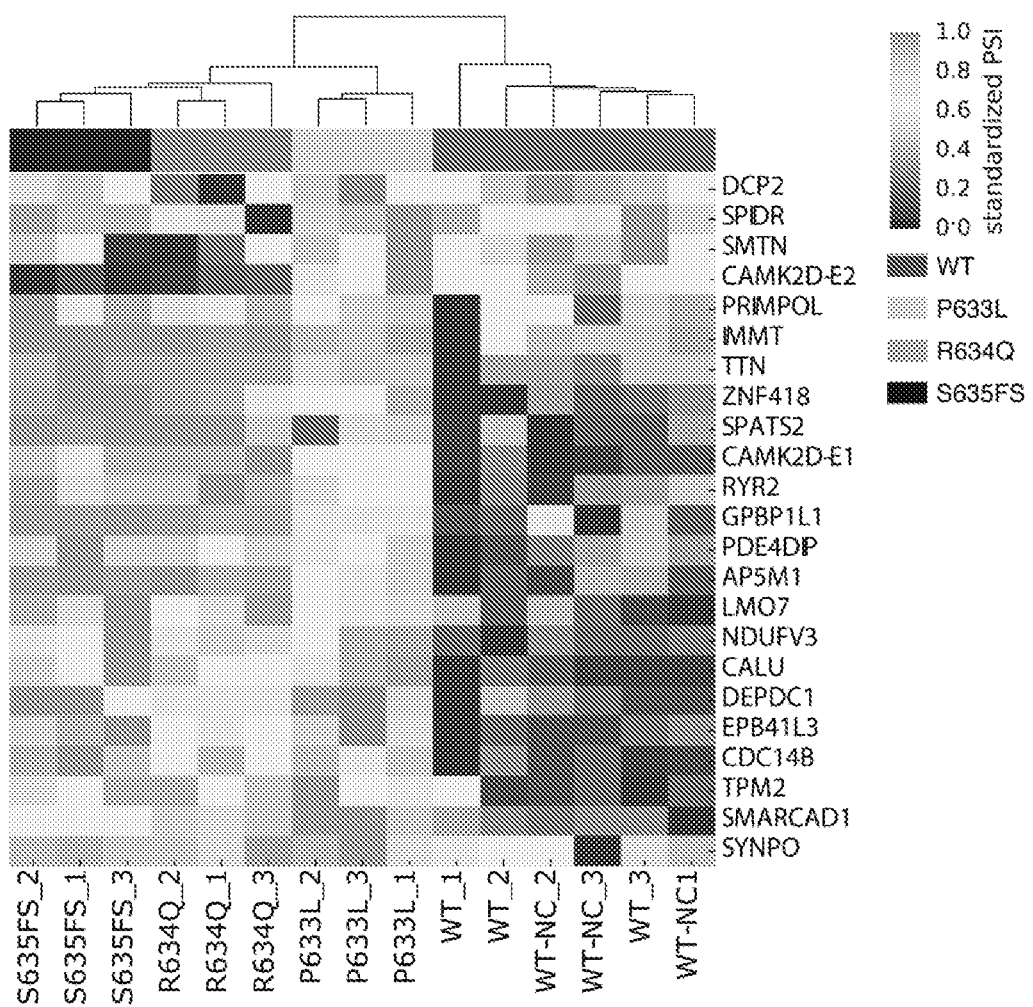
FIG. 2A shows a heat map of PSI values for gene affected by RBM20 mutations. For TTN only the most affected exon is displayed.
Figure 2B:
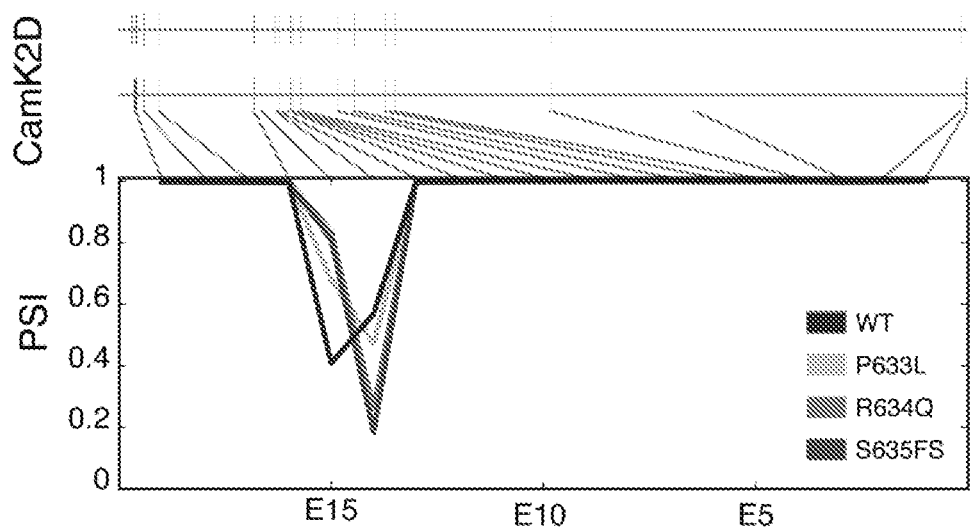
FIG. 2B shows a PSI plot of CamK2D.

To evaluate the impact of the P633L mutation on RBM20-dependent splicing we performed RNA-seq on the iPSC-CMs from each genotype. Alternative splicing events were inferred from the RNA-seq data with a combination of DEXSeq and PSI calculations. As shown in FIG. 2A all the WT lines clustered together independently of whether they went through the genome editing process. All the mutant lines clustered together although the P633L mutation has an overall less dramatic effect on splicing. RT-PCR confirmations for TTN and RyR2 altered splicing are shown in FIG. 6.

Impaired Function of RBM20 Mutated Cardiomyocytes

Figure 2C:
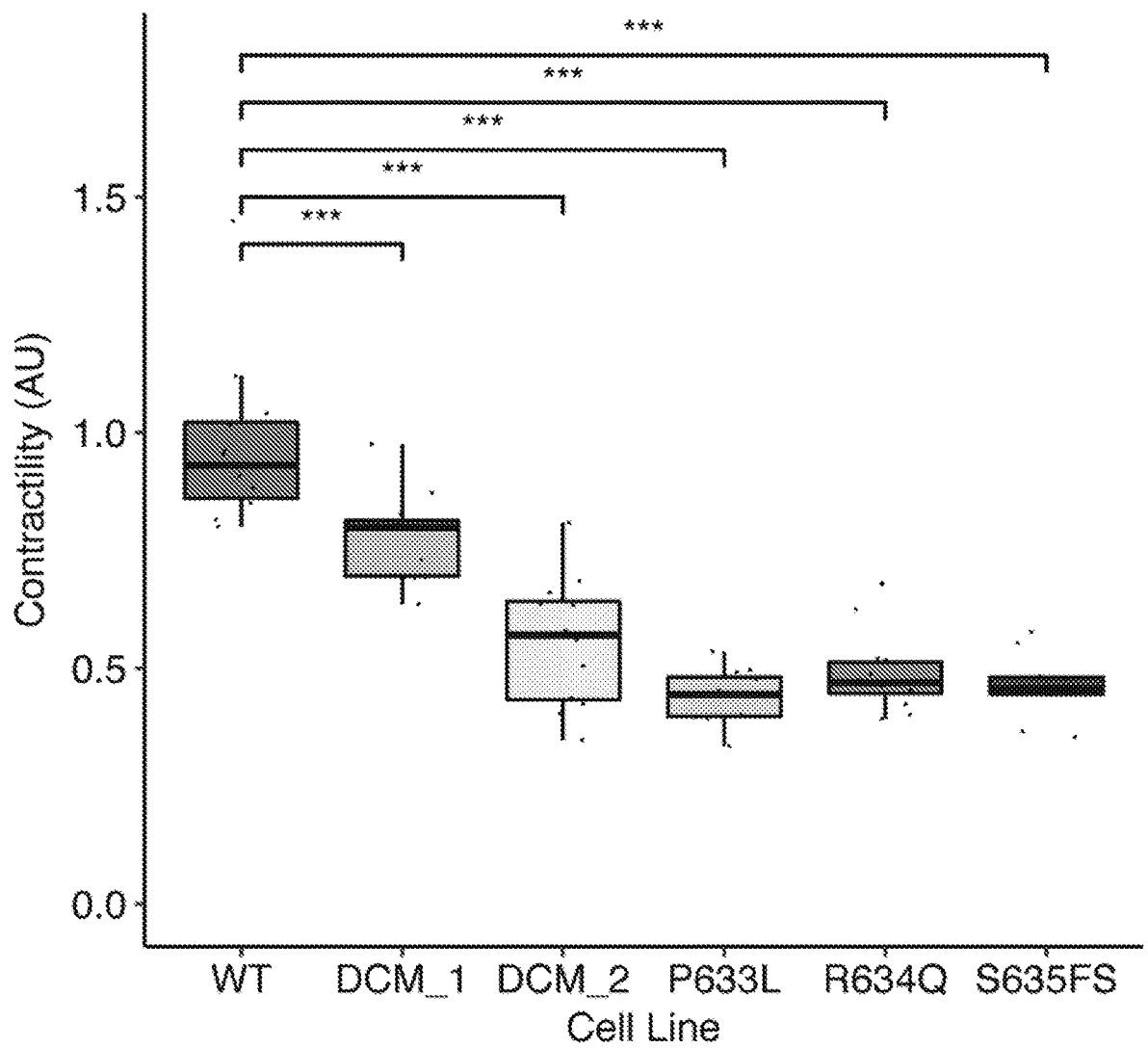
FIG. 2C shows a time-series-based analysis of contractile profiles of RBM20 WT and mutant iPSC-CMs. The values of WT iPSC-CMs were normalized to 1. Student's t-test was used to evaluate the difference between WT and RBM20 mutant iPSC-CMs (n=12).
Figure 2D:
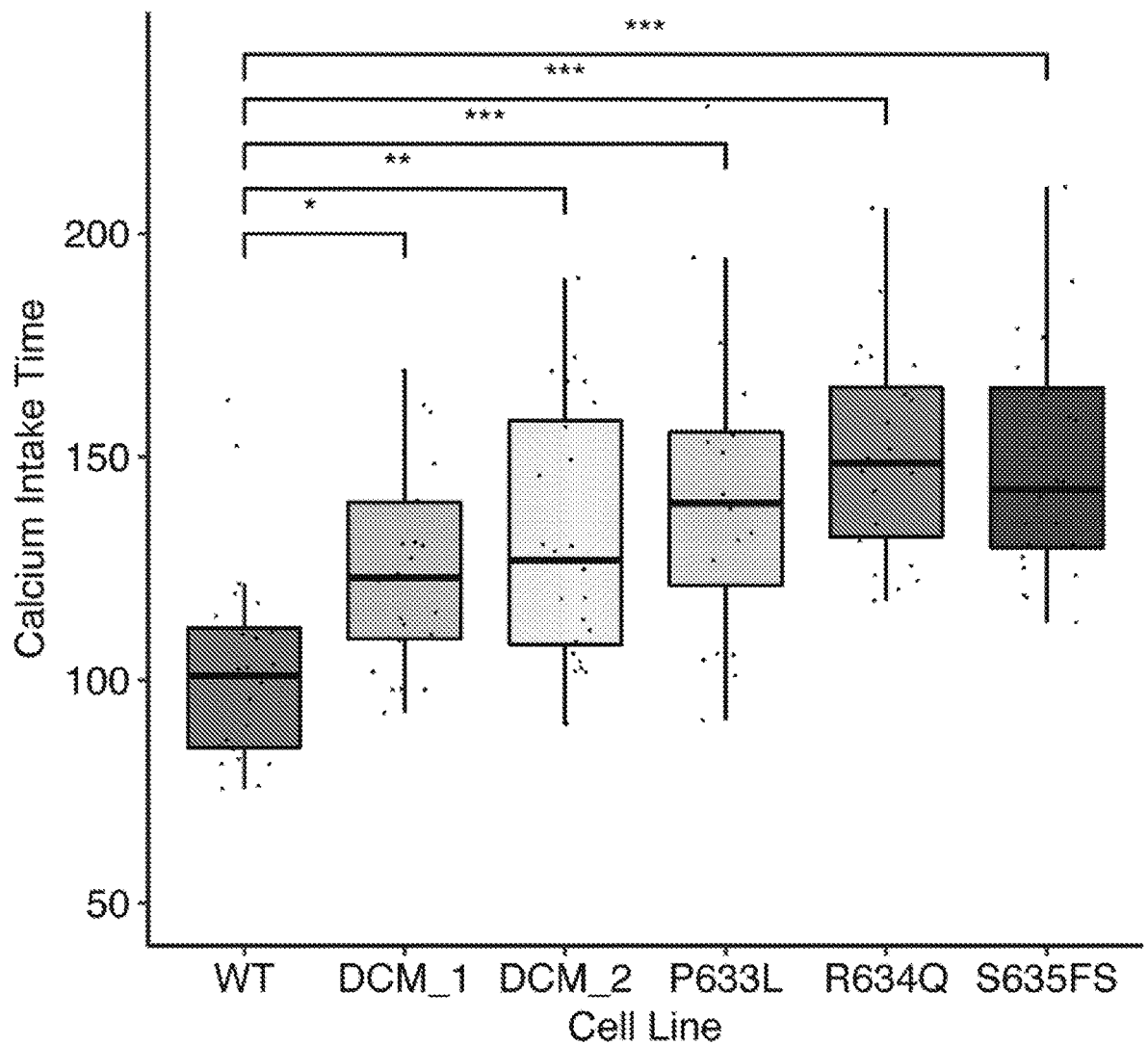
FIG. 2D shows a time-series-based analysis of calcium transients. Upstroke time is the calcium influx time in WT and RBM20 mutant iPSC-CM (n=18). (* padj<0.05,  padj<0.01, * padj<0.001, where padj is adjusted p-value)

DCM patients exhibit a significant reduction in left ventricle fractional shortening during systole[5]. To evaluate whether the P633L mutation causes a clinically relevant phenotype in our system, the cells were assayed for contractility. As shown in FIG. 2C, all the mutant lines showed a reduction in contractile function as measured by maximum displacement at systole. It has been proposed that a reduced calcium release from the sarcoplasmic reticulum leads to impaired heart contraction[18]. Many of the RBM20 targets are involved in calcium handling. To test whether calcium handling was altered in the RBM20 mutants, we assayed the iPSC-CMs for calcium transients. We show that the calcium influx is significantly slower in the mutated lines (FIG. 2D).

Retinoic Acid Upregulates RBM20 Expression

Figure 3A:
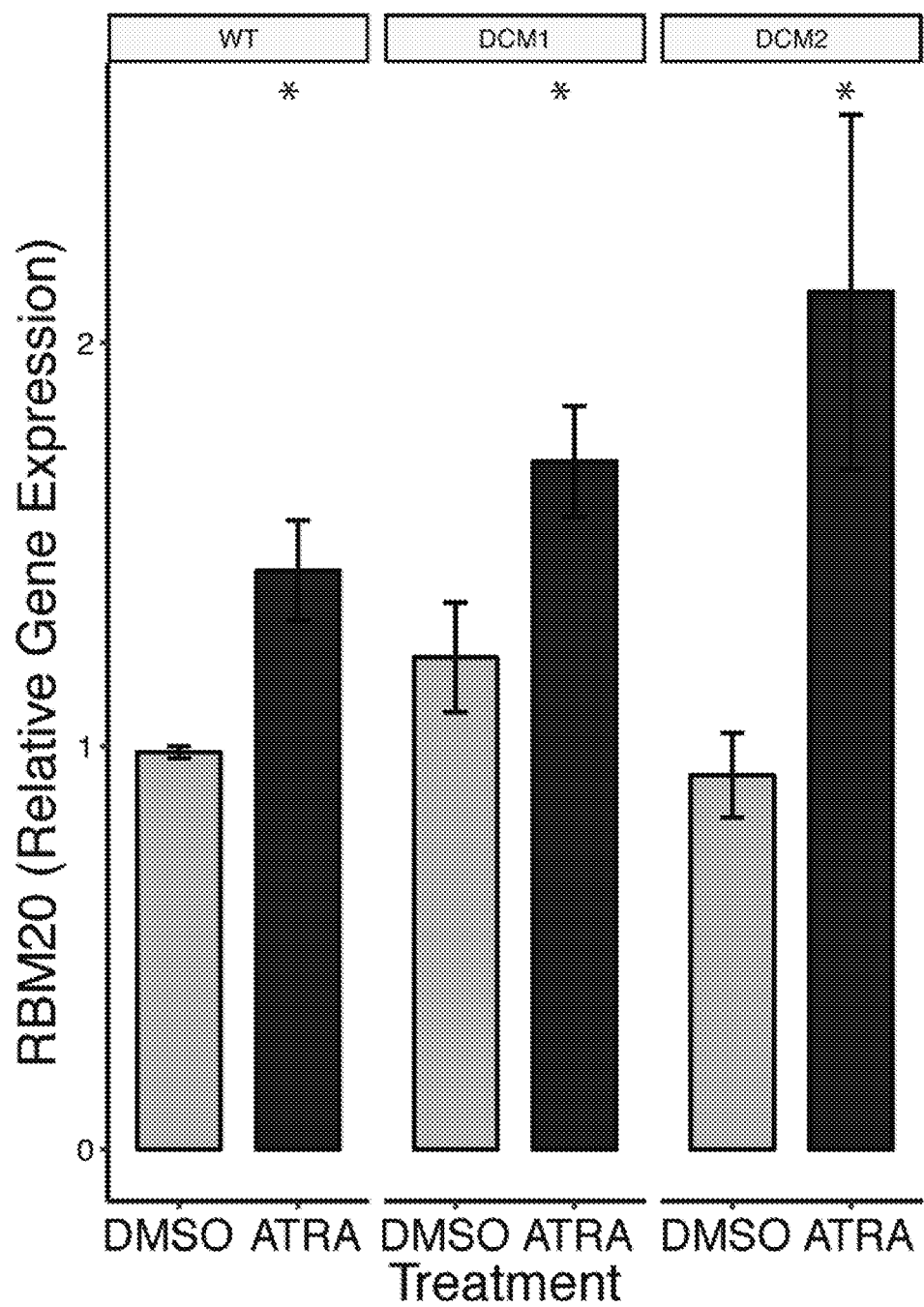
FIG. 3A shows relative gene expression measured by qRT-PCR for RBM20 upon treatment with different doses of ATRA. TBP is used as endogenous control.

We hypothesized that transcriptional upregulation of RBM20 could be a therapeutic strategy to compensate for the loss of function of the mutated allele. We interrogated the gene Expression Atlas[19] for conditions that lead to upregulation of RBM20 in any cell system. We found that ATRA was associated with upregulation of RBM20 expression in human embryonic stem cells[20]. To confirm the effect of ATRA on RBM20 expression in iPSC-CM, we treated iPSC-CMs with ATRA. FIG. 3A shows upregulation of the RBM20 transcript upon treatment with ATRA in WT and DCM iPSC-CM.

Upregulation of RBM20 is Sufficient to Revert Splicing Defects in iPSC-CM

Figure 3B:
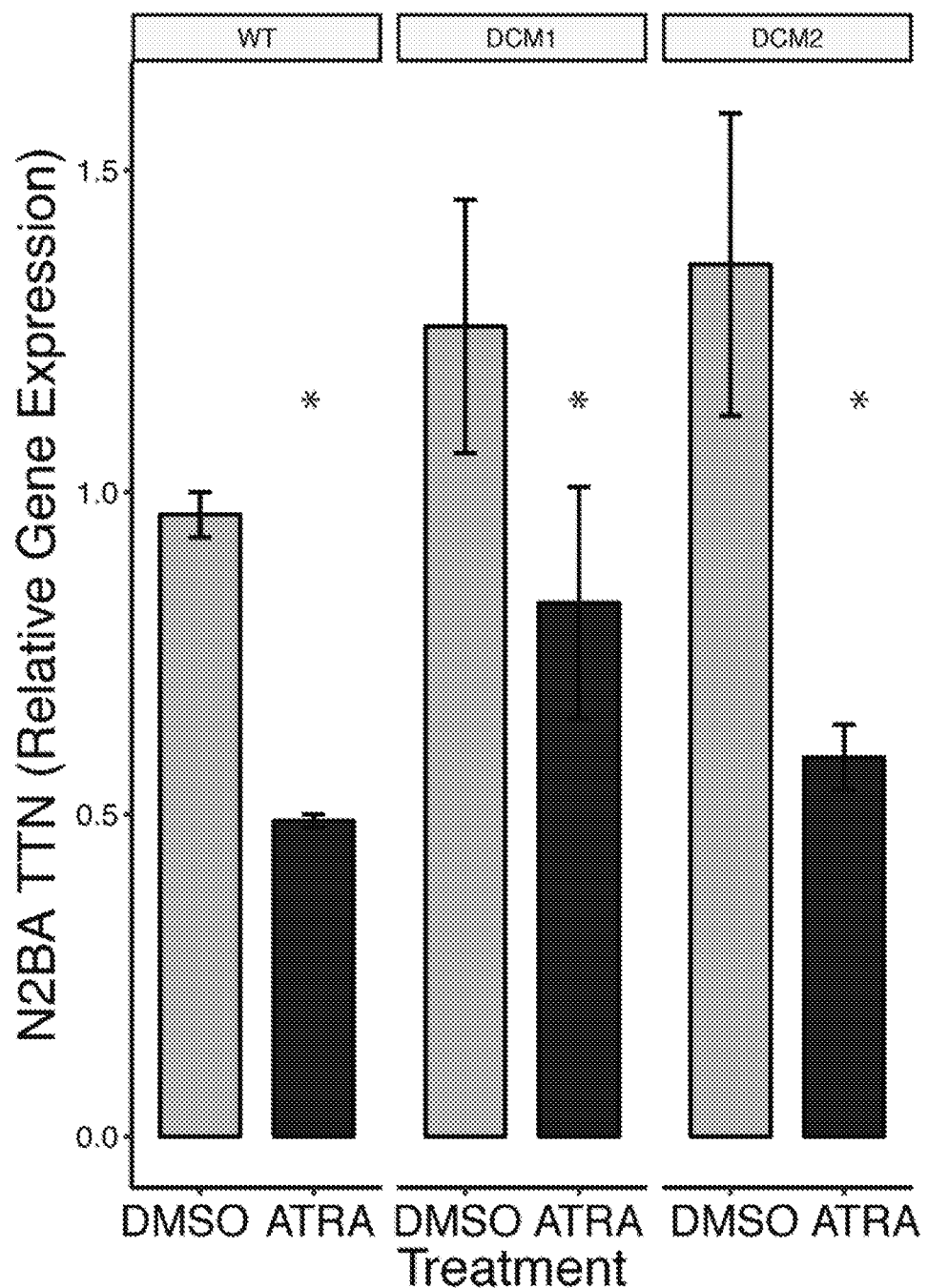
FIG. 3B shows RBM20 and TTN expression upon ATRA treatment in WT and patient derived iPSC-CM.

To evaluate the effect of ATRA in patient-derived cells, we derived iPSC-CM from father and son from our studied family and treated them with ATRA. In all lines, a 48 hours ATRA treatment resulted in moderate but consistent upregulation of the RBM20 transcript (FIG. 3A) and downregulation of the aberrant splicing in TTN (FIG. 3B), one of the known target genes of RBM20.

Functional Consequences of ATRA Treatment

Figure 3C:
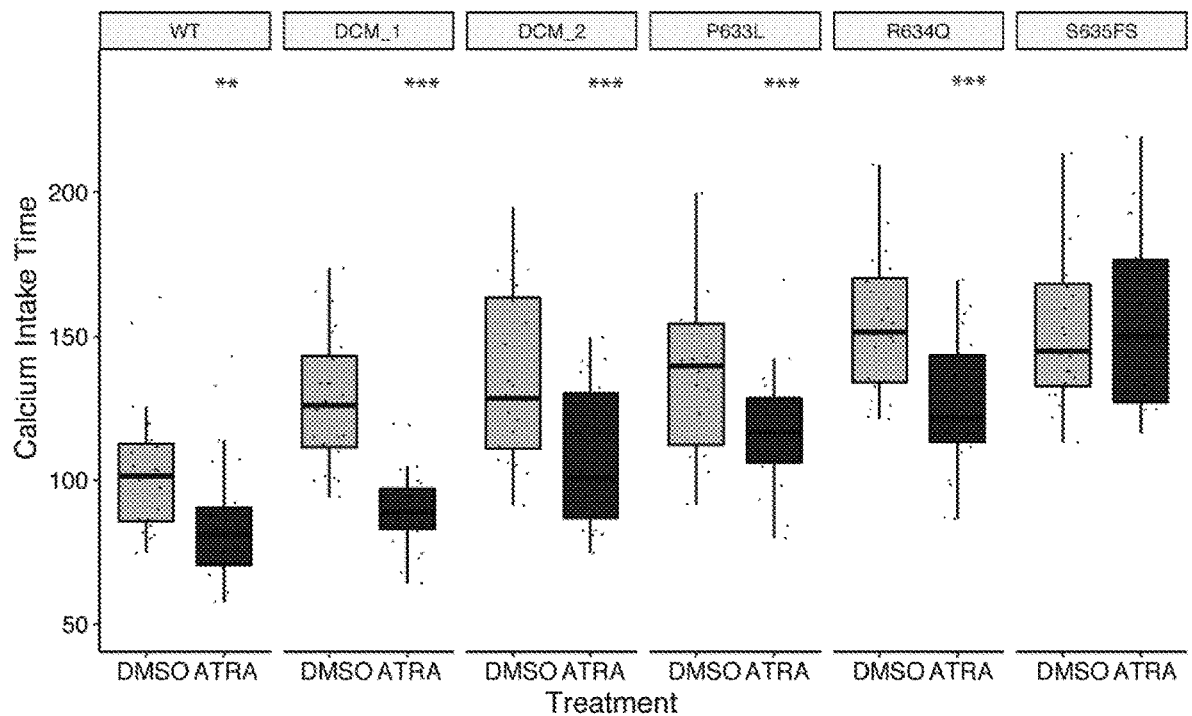
FIG. 3C shows time-series-based analysis of calcium transients upon ATRA treatment. Upstroke time is the calcium influx time (n=15-18).
Figure 3D:
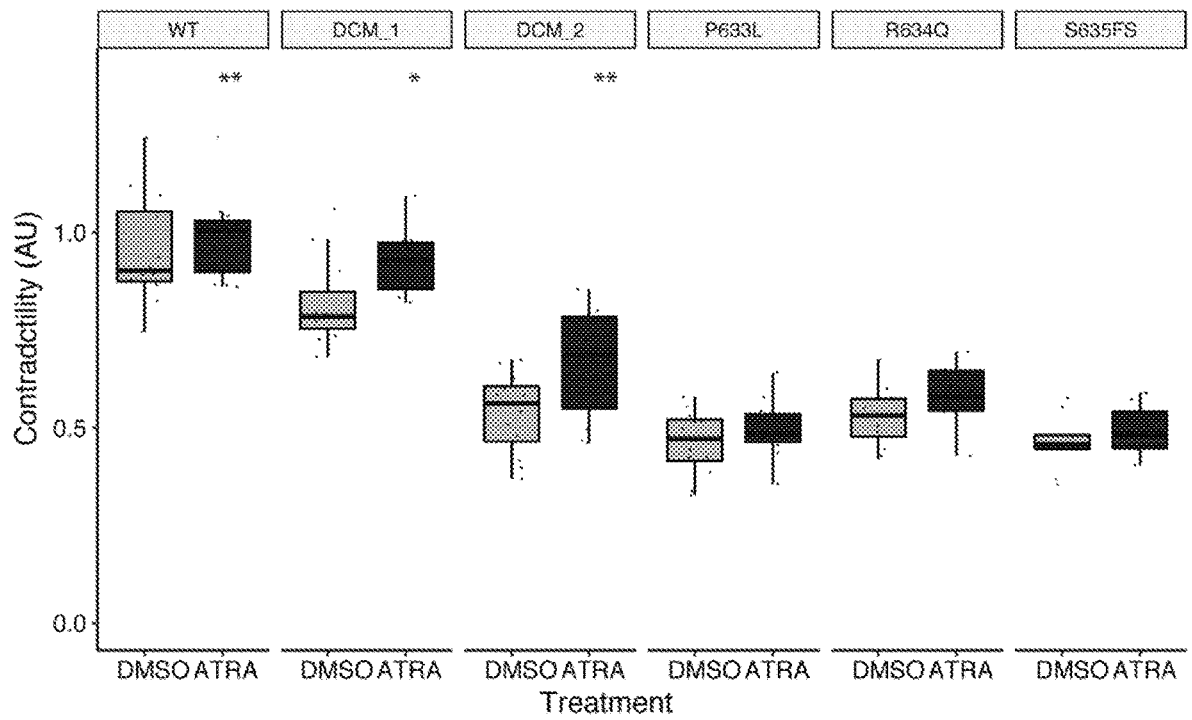
FIG. 3D shows time-series-based analysis of contractile profiles of RBM20 WT and mutant iPSC-CMs upon ATRA treatment. The values of WT iPSC-CMs at baseline were normalized to 1.

Finally, we tested whether ATRA-mediated correction of the splicing defects would result in functional amelioration of the DCM phenotype. As shown in FIG. 3C, upon 72 hours ATRA treatment, iPSC-CMs derived from father and son showed a dose-dependent reduction of calcium influx time. This lead to a correction of the calcium influx time to a level similar to WT in the case of the son, our proband. A similar, but much smaller effect is observable in the homozygous engineered isogenic lines, P633L and R634Q (although not significant for this sample). Finally, no response was observed in the S635FS (FIG. 4A). Because this mutation produces a premature stop codon, resulting in a KO, the lack of rescue in this line suggests that the improved phenotype observed upon ATRA treatment is RBM20 dependent. In parallel with the reduction in calcium influx time, upon 72 hours ATRA treatment DCM_1 and DCM_2 iPSC-CM display a significant increase in contractile capacity (FIG. 3D). This is also RBM20-dependent as the KO iPSC-CM does not restore this function.

Methods

Human Samples

The iPSC lines form the proband and his father (DCM_1 and DCM_2 respectively) were derived under the IRB-30064 from blood cells using a non-integrating Sendai virus. Participants gave written informed consent. Control iPSC line was obtained from the Stanford Cardiovascular Institute Biobank.

Linkage Analysis in a Family with Familial DCM

Exome sequencing for the proband, his father and his mother was obtained from blood cells. The reads were mapped to the human genome reference GRCh37. Single Nucleotide Variants (SNVs) and INDELs were called and filtered following the best practice of GATK (v3) and further annotated using ANNOVAR (v2015Dec14). To prioritize these variants, we took the following filtering strategies. First of all, we checked whether the mutation had already been reported in dbSNP database. If it is in the database, we further checked whether it had been annotated by ClinVar and what kind of effect it was classified, such as pathogenic, likely pathogenic, benign, or likely benign, etc. If it is not reported in dbSNP yet, we calculated the mutation frequency in the ExAC database, with the guideline that the frequency higher than 5% in the normal population is less likely to be causing in this disease. Second, we filtered these variants based on the position (coding versus non-coding regions) and whether the mutations resulted in a missense, formation of premature stop codon, or a silent change in the protein sequence. Finally, we focused pour analysis on the heart development or heart disease related genes (101 genes).

Genome Editing

Sqrna Design and Cloning

The single guide RNA was designed using the Feng Zhang's lab CRISPR Design tool (crispr.mit.edu). The two complementary oligonucleotides were ordered separately, annealed in T4 ligation buffer (NEB), and phosphorylated with T4 PNK (NEB). The annealed and phosphorylated oligos were cloned into the BbsI sites of the pSpCas9(BB)-2A-GFP plasmid and transformed in STBL3 E. coli cells. The clones' sequence was confirmed by Sanger sequencing.

Genome Editing in Human iPSC

Human iPSCs were plated into Matrigel coated 6-well plates 1 day before transfection at low density in E8 media. On the day of transfection, the cells were supplied with E8 media supplemented with Rock inhibitor. The cells were transfected with Lipofectamine 3000 following manufacturer's instruction. 1 µg of CRISPR/Cas9 vector (pSpCas9 (BB)-2A-GFP) and 4 µg of ssDNA donor were used for each well of a 6-well plate. GFP+ cells were isolated 36-48 hours after transfection using a FACSAria flow cytometer with a 100-µm nozzle. Cells were plated at density of $2-3 \times 10^3$ cells/well in a 6-well plate in E8 media supplemented with Rock inhibitor. Cells were maintained in E8 media supplemented with Rock inhibitor for the first 3 days, then they were cultured in regular E8 media until the colonies reached a size of ~0.5 mm. Individual iPSC clones were isolated with the assistance of a stereomicroscope located inside a cell culture cabinet and each re-plated in a well of a 24-well plate in E8 supplemented with Rock inhibitor. A few cells for each clone were resuspended in 20 µl media and used for genomic DNA isolation with 0.5 µl of DNA Release Additive in 20 µl Dilution Buffer (Phire Animal Tissue Direct PCR Kit (Thermo Fisher)). 2 µl of this mix was used for direct PCR amplification of the target genomic region using Prime-STAR GXL DNA Polymerase (Clontech).

Oligos
The oligos for the sgRNA cloning:
Fw_Guide2:
(SEQ ID NO: 1)
CACCGCTCACCGGACTACGAGACCG Rv_Guide2:
(SEQ ID NO: 2)
aaacCGGTCTCGTAGTCCGGTGAGC The lower-case letters represent the overhang nucleotides for the cloning.

The following sequence was used as donor:
>R634Q_KI_donor
(SEQ ID NO: 3)
TGTGGGACCTCGGGGAGAGTGACCGGCTCACCGGACTACGAGACtGCGGC

CTTTCTGGGCCATATCTGTGAGGGAGCCAAGGAGCAGGATTTAGAATCTT

CACACCTCCCATCCCACCCCACCCACA

The lower-case letter represents the mutation.

For PCR amplification:
>RBM20_Fw
(SEQ ID NO: 4)
CTGGACTAGGGCAATCTTGCCC

>RBM20_Rev
(SEQ ID NO: 5)
CTCATTCTGCTTGGCCTTGGCG

Cardiomyocytes Differentiation

The iPSCs were differentiated into cardiomyocytes as a monolayer and through the modulation of Wnt signaling as previously described (Burridge et al. Chemically Defined Culture and Cardiomyocyte Differentiation of Human Pluripotent Stem Cells. In: Current Protocols in Human Genetics. 2015. p. 21.3.1-21.3.15; herein incorporated by reference). Briefly, iPSCs were plated at low density on matrigel coated plates to have them 70-80% confluent after 4 days (Day 1 of differentiation) when differentiation was induced with RPMI supplemented with 1×B27 Minus Insulin (Life Technologies 0050129SA) and 6 µM CHIR (TOCRIS 4953). On day 4 media was replaced with RPMI supplemented with 1×B27 Minus Insulin and 5 µM IWR (Selleckchem S7086). On day 6 media was replaced with RPMI supplemented with 1×B27 Minus Insulin. From day 8 to day 12 cells were kept in RPMI supplemented with 1×B27 and then switch to starvation media (RPMI-Glucose supplemented with 1×B27). Then the cells were replated at a density of 2.5 Mi cells/well. From day 24 cells were treated with Maturation Media (MM) for at least 3 weeks before being used for experiments.

RNA Seq

Two months old cardiomyocytes from 3 independent differentiation were collected and RNA was purified using TRizol extraction and isopropanol precipitation. 2-10 ng of total RNA were reverse transcribed to full-length complementary DNA using SmartSeq2 method (Picelli et al. Full-length RNA-seq from single cells using Smart-seq2. Nat Protoc. 2014; 9:171-181). Then 100-200 pg of full-length cDNA were tagmented to fragments with a median length of 500 bp and added sequencing index using Illumina Nextera XT kit as described by manufacture protocol. Multiple samples with different sequencing index were pooled and sequenced on an Illumina HiSeq. RNA-Seq reads were mapped to GRCh38 using STAR v2.5.1b (Dobin et al. STAR: ultrafast universal RNA-seq aligner. Bioinformatics. 2012; 29:15-21). Gene level expression matrix was collected with featureCounts v1.6.0 (Liao et al. featureCounts: an efficient general purpose program for assigning sequence reads to genomic features. Bioinformatics 2014; 30:923-930). For each exon we define inclusive and exclusive reads. Inclusive reads are those reads that include the exon of interest. Exclusive reads are reads that include both the upstream and the downstream exon but not the exon of interest. Inclusive and exclusive reads were counted directly from the bam files using a custom script. Percentage of Spliced-In (PSI) is the ratio between inclusive reads over the sum of inclusive and exclusive reads. We detected alternative splicing with DEXSeq v1.16.10 (Anders et al. (2012) Detecting differential usage of exons from RNA-seq data. Genome Res. 22:2008-2017). We only included exons with at least 64 counts on average. We considered an exon to be alternatively spliced when DEXSeq padj<0.05 and PSI>0.1.

qRT-PCR

To analyze the transcript isoforms, Reverse Transcription was performed on 500 ng of total RNA using SuperScript VILOTM cDNA Synthesis Kit (Life Technologies) following manufacturer's instructions. PCR was performed using PrimeSTAR GXL DNA Polymerase from Takara Bio. quantitative RT-PCR (qPCR) was performed using Biorad SYBR Green Master Mix.

Comparison between two group was performed using Wilcoxon test. For comparisons with more than two groups the Kruskal-Wallis test was used.

Image Acquisition

For imaging experiments cells were dissociated and plated onto Matrigel-coated 384-well tissue culture plates (Greiner Bio-One) at a density of 20,000 cells/well and let recover for 4 day changing media every second day. All cell manipulations were conducted in a cell culture cabinet on a 37° C. dry heat block and all the solutions were preventively warmed to 37° C. to prevent temperature fluctuation. Cells were washed 4 times with Fluorobrite. For contractility analysis the cells were loaded for 15 min with Hoechst 33258 (H3569, Life Technologies) to 4 µg/ml and wheat germ agglutinin-Alexa Fluor 488 conjugate (W11261, Life Technologies) to 10 µg/ml for contractility analysis in Fluorobrite. For calcium analysis the cells were loaded for 20 min with Hoechst 33258 and 2.7 µM Fluo-4NW in Fluorobrite. After the fluorophore loading the cells were washed 4 more times before image acquisition. Time series images were acquired automatically using the IC200 KIC instrument (Vala Sciences, California, USA) at an acquisition frequency of 100 Hz for a duration of 10s, with excitation wavelength of 485/20 nm and emission filter 525/30 nm using a 0.75 NA 20× Nikon Apo VC objective. A single image of the Hoechst was acquired after the time series.

Image Analysis and Calculation of Physiological Parameters

The image analysis and physiological parameter calculation was conducted using commercially available Cyteseer (Vala Sciences) as previously described (Cerignoli et al. High throughput measurement of $Ca^{2+}$ dynamics for drug risk assessment in human stem cell-derived cardiomyocytes by kinetic image cytometry. J Pharmacol Toxicol Methods. 2012; 66:246-256). Contractility analysis was performed using a custom Matlab script. Data tables were analyzed using R. Comparisons between multiple groups were evaluated for significance using two way ANOVA to remove the batch effect, followed by multiple comparison of mean using the Tukey's test.

Discussion

In a family with familial DCM, we identified a new variant in RBM20 and evaluated its effect on cardiac specific splicing. We detected aberrant splicing of previously described RBM20 targets in the P633L mutant iPSC-CMs, as well as a functional defect in their contractility and calcium handling. Evidence suggests that RBM20 mutations act through a haploinsufficiency mechanism: higher expression of RBM20 correlates with more spliced targets; lower RBM20 expression in patients correlates with splicing defects similar to those observed in RBM20 mutant[21]; RMB20 mutation loses interaction with other spliceosomal proteins[10]; and in the rat model the homozygote has a more severe phenotype than the heterozygote[22]. All the patients with RBM20 mutations described so far are heterozygous, they have one fully functional copy of RBM20. We reasoned that this may offer an opportunity for drug development as the upregulation of the endogenous RBM20, and any residual functional activity of the mutant, would be beneficial. For example, doubling the expression of RBM20 in haploinsufficient tissues where the mutant allele retains no activity would restore the levels of the protein to wild-type. Similar approaches of gene expression upregulation in haploinsufficiency have been beneficial in disease model of Dravet syndrome[23] and vascular stenoses[24]. Here, we identified ATRA as a small molecule that upregulates RBM20 in a dose-dependent manner in iPSC-CMs. The mild upregulation of RBM20 was sufficient to at least partially revert the splicing defect in vitro and to mitigate cellular phenotypes. The mechanism of action of ATRA is unclear at this point. No retinoic acid responsive element is present in the promoter region of RBM20, suggesting an indirect effect. The beneficial effect of ATRA on molecular and cellular phenotypes is RBM20 dependent—no improvement is observed in the S635FS mutant (FIGS. 3D and 4D).

Previous studies of DCM causing mutations have been based on analyses of large cohorts of patients and large pedigrees to follow segregation of genomic variants and disease over several generations. Experimental confirmation of these variants' pathogenic effect was obtained using artificial reporter genes/overexpression. The use of genome editing technologies in combination with in vitro differentiation of human iPSC to evaluate pathogenicity of new variants is emerging as a new promising tool. Its value has recently been shown by a study of variants related to channelopathy[25]. We show the first use of this technology to assess the pathogenicity of a new DCM-causing mutation in RBM20.

RBM20 is a tissue specific splicing regulator, highly expressed only in heart and found at lower level in skeletal muscle. Mutations in RBM20 are associated with a clinically severe form of DCM[6,21] and with a few exceptions cluster in a highly conserved SR rich region. We identify a new mutation adjacent to this previously reported mutation hotspot. This is a Proline to Leucine transition. Prolines are rigid amino acids, usually excluded from canonical alpha helices and beta sheets and located at their end to impose an interruption in the ordered structure. SR domain are involved in both protein-protein interaction and regulation of subcellular localization and are usually unstructured. Although the proline 633 may not be directly involved in the protein-protein interaction, it may control the orientation of the unstructured loop containing the SR domain influencing both interaction with other splicing proteins and recognition by kinase and/or phosphatases impacting the subcellular localization[26].

Figure 6A:
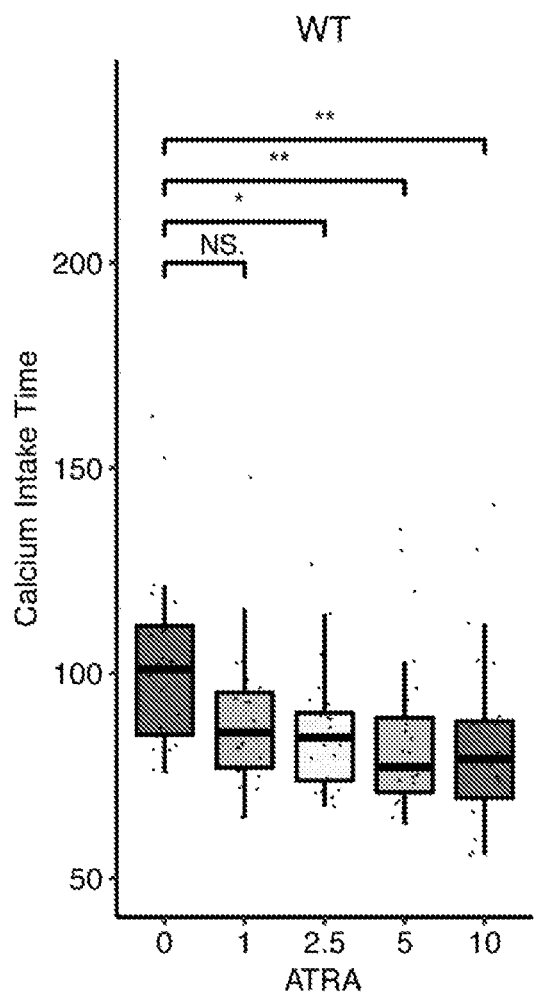
FIGS. 6A-6L show a dose response curves of iPSC-CMs calcium handling and contractile activity upon ATRA treatment.
Figure 6B:
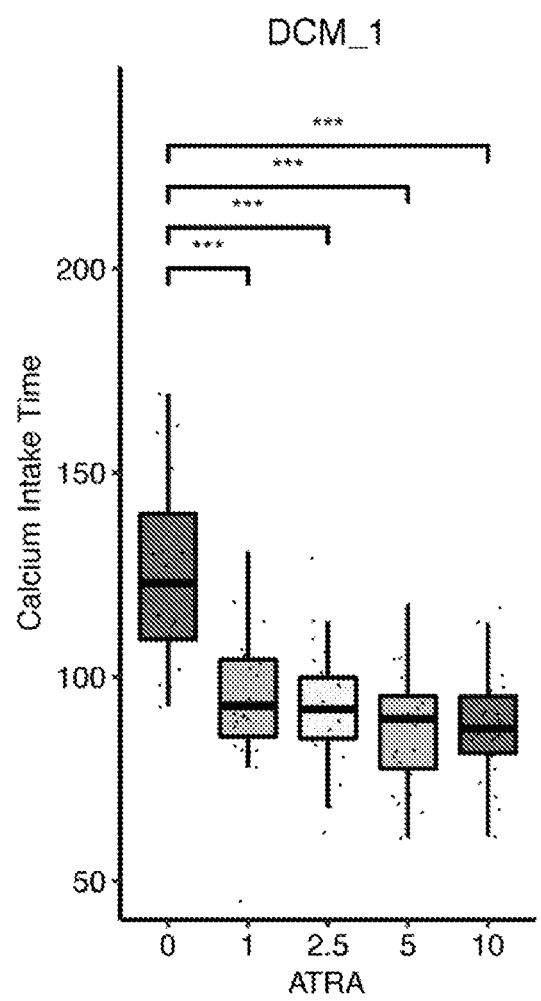
Figure 6C:
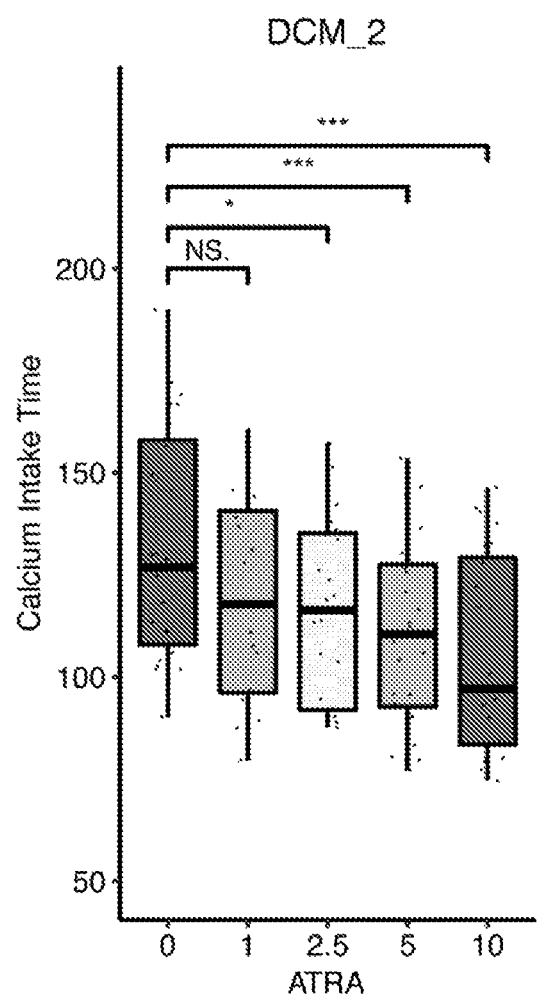
Figure 6D:
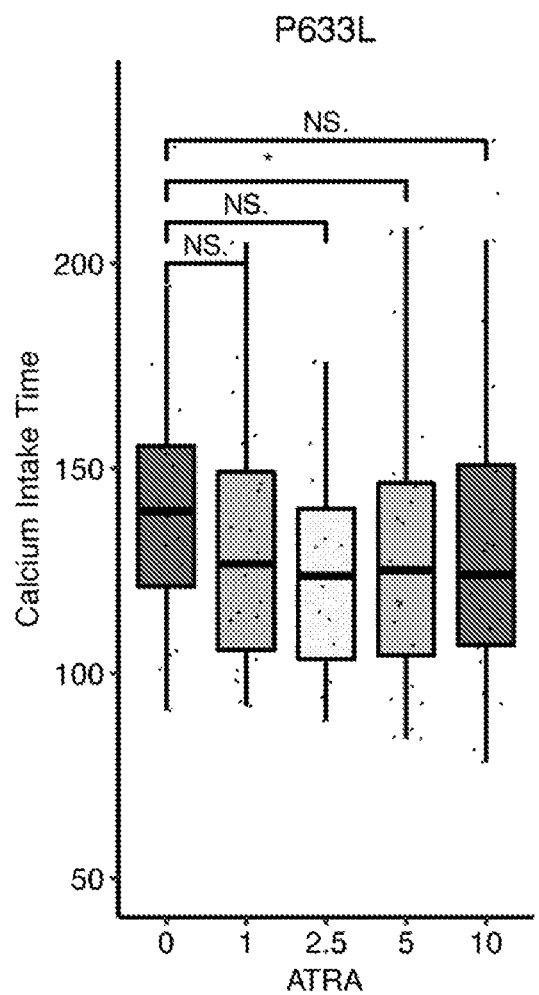
Figure 6E:
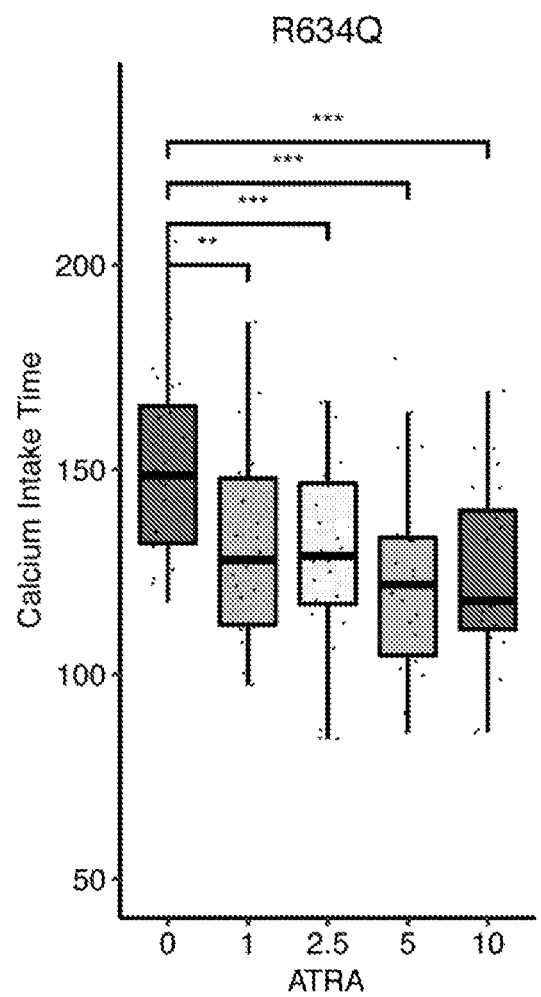
Figure 6F:
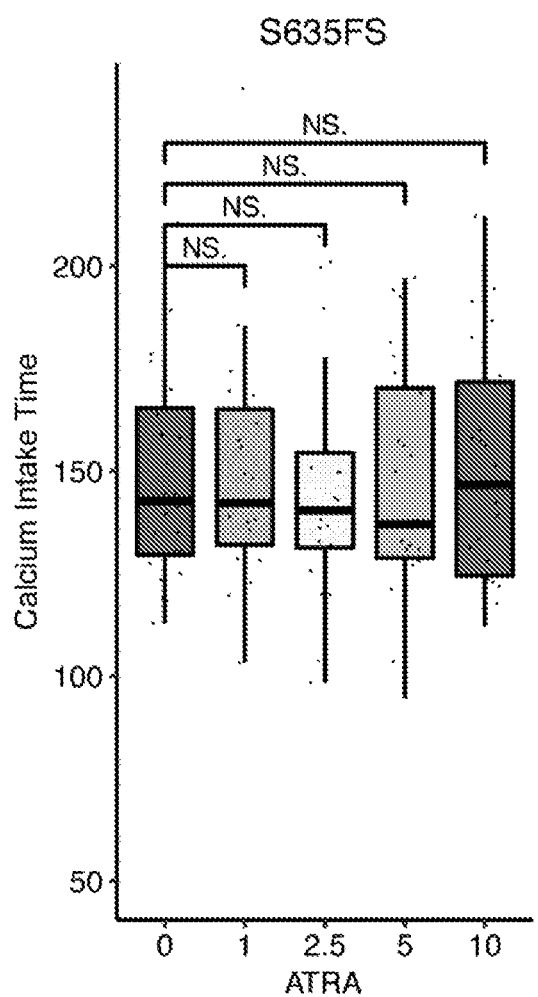
Figure 6G:
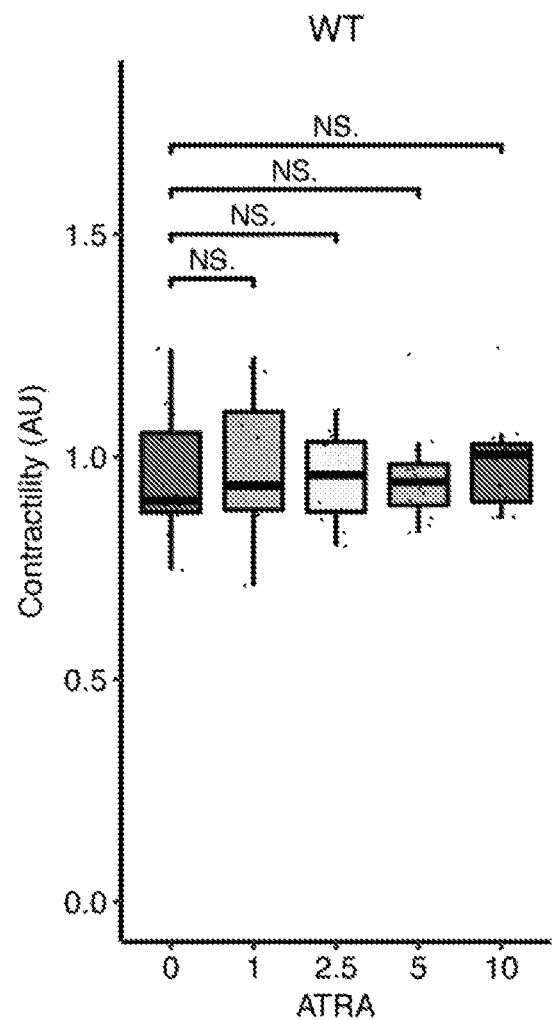
Figure 6H:
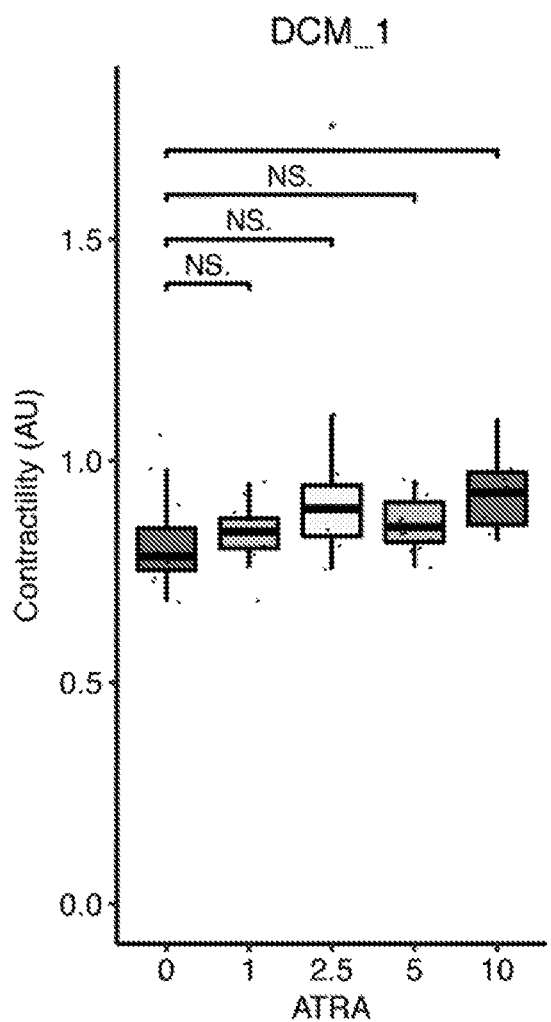
Figure 6I:
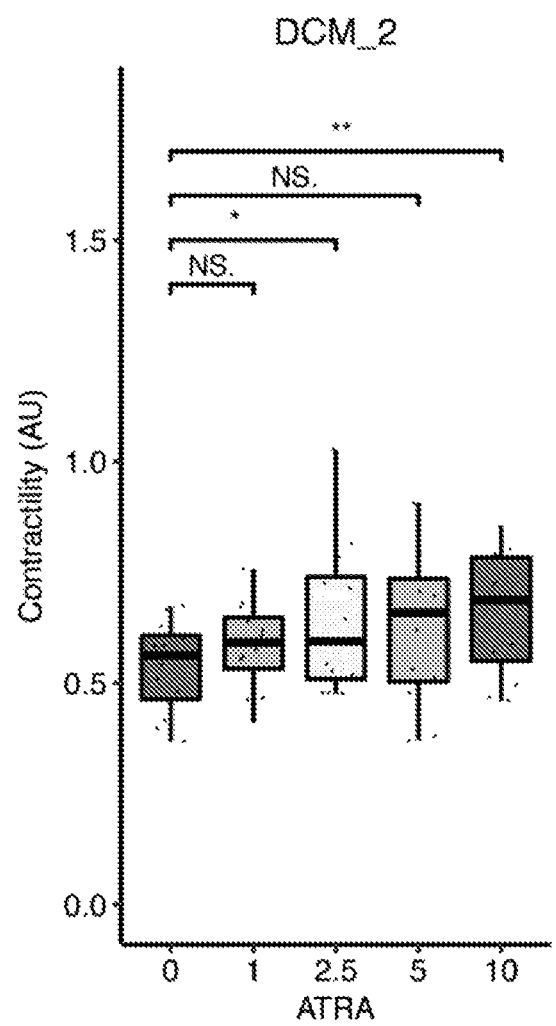
Figure 6J:
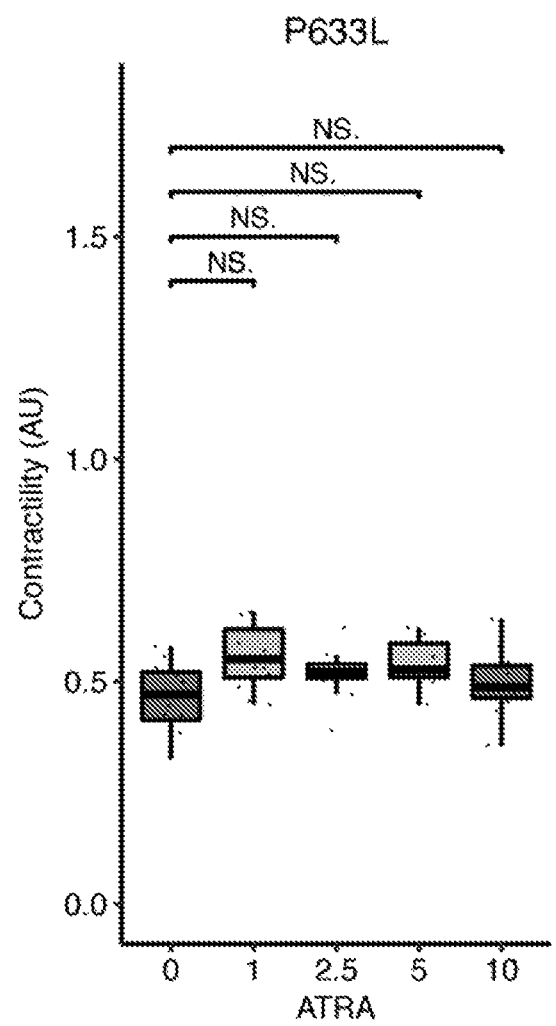
Figure 6K:
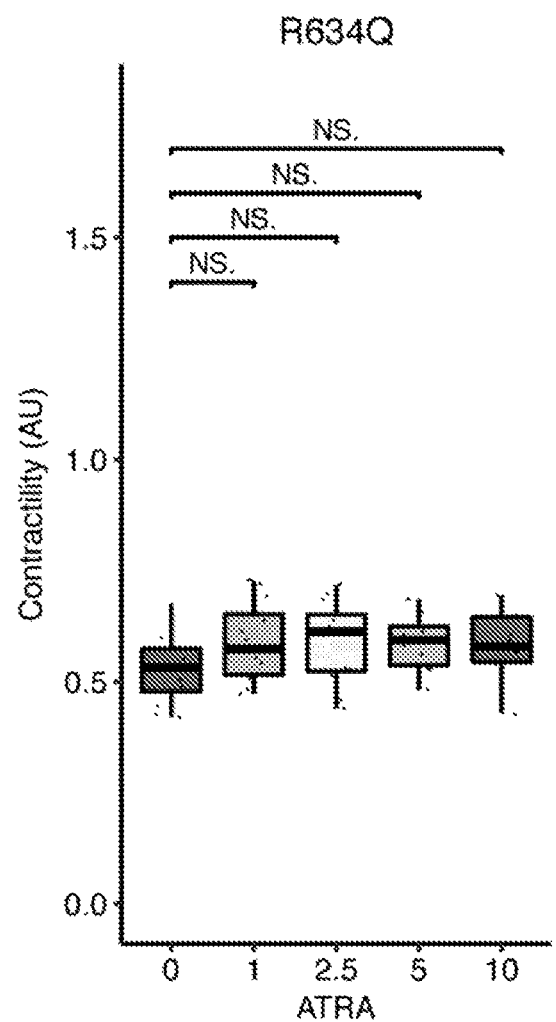
Figure 6L:
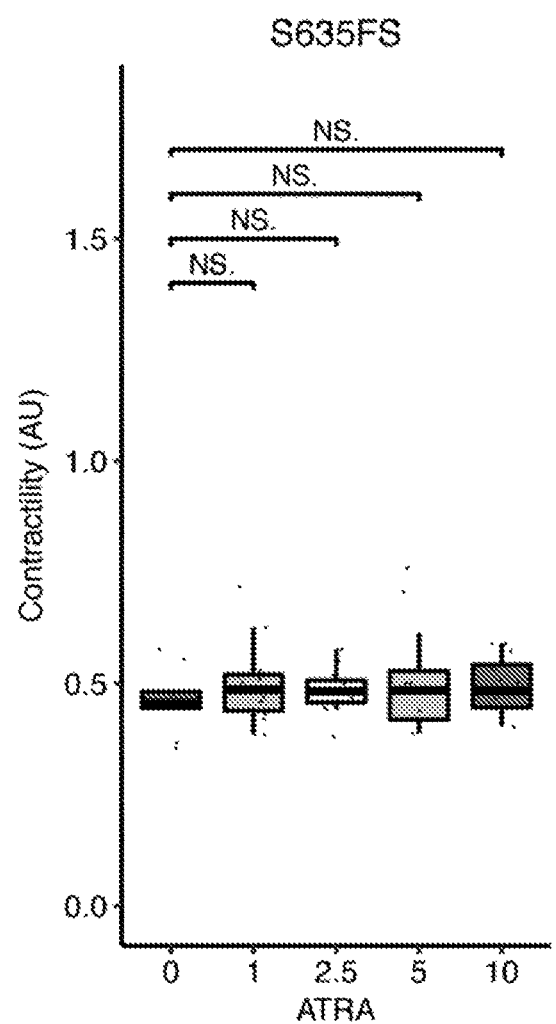

Calcium mishandling in RBM20 mutant cardiomyocytes has been previously reported and attributed to the function RBM20 as a splicing-regulator of several calcium handling genes[27,28] Limitations of previous studies include the lack of isogenic controls, significant differences in beat rate between different lines, and the functional immaturity of iPSC-CM. In particular iPSC-CMs usually rely on calcium influx form the extracellular space. In adult cardiomyocytes 70% of the calcium triggering the contraction comes from the sarcoplasmic reticulum (SR)[29]. We believe that this has been a main limitation of previous studies on RBM20 mutant cardiomyocytes. RyR2 plays a major role in the release of calcium from the SR during cardiac contraction. It has been previously described to be mis-spliced in RBM20 mutant and we confirm this in this manuscript (FIGS. 6A and B). The functional consequences of this aberrant splicing may have been underestimated because of the inadequacy of the system. We used a newly developed protocol to induce maturation of iPSC-CMs which allowed us to uncover different dynamics in calcium influx in RBM20 mutant compared to WT control.

In this manuscript, we developed a pipeline for using genome editing and differentiation of iPSCs to generate personalized in vitro diseases models. We used the pipeline to generate a model that allowed us to uncover molecular and cellular phenotypes relevant to DCM pathogenesis and to test a new therapeutic approach. We showed that upregulation of RBM20 is a potential therapeutic strategy for RBM20-deficint DCM and that ATRA upregulates RBM20 and reverts DCM phenotypes in vitro.

REFERENCES

1. Yancy C W, Jessup M, Bozkurt B, Butler J, Casey D E Jr, Drazner M H, Fonarow G C, Geraci S A, Horwich T, Januzzi J L, Johnson M R, Kasper E K, Levy W C, Masoudi F A, McBride P E, McMurray J J V, Mitchell J E, Peterson P N, Riegel B, Sam F, Stevenson L W, Tang W H W, Tsai E J, Wilkoff B L. 2013 ACCF/AHA guideline for the management of heart failure: executive summary: a report of the American College of Cardiology Foundation/American Heart Association Task Force on practice guidelines. *Circulation.* 2013; 128:1810-1852.
2. Japp A G, Gulati A, Cook S A, Cowie M R, Prasad S K. The Diagnosis and Evaluation of Dilated Cardiomyopathy. *J Am Coll Cardiol.* 2016; 67:2996-3010.
3. McNally E M, Mestroni L. Dilated Cardiomyopathy: Genetic Determinants and Mechanisms. *Circ Res.* 2017; 121:731-748.
4. Wilcox J E, Hershberger R E. Genetic cardiomyopathies. *Curr Opin Cardiol.* 2018; 1.
5. Hershberger R E, Morales A, Siegfried J D. Clinical and genetic issues in dilated cardiomyopathy: a review for genetics professionals. *Genet Med.* 2010; 12:655-667.
6. Li D, Morales A, Gonzalez-Quintana J, Norton N, Siegfried J D, Hofmeyer M, Hershberger R E. Identification of Novel Mutations in RBM20 in Patients with Dilated Cardiomyopathy. *Clin Trans/Sci.* 2010; 3:90-97.
7. Lund L H, Khush K K, Cherikh W S, Goldfarb S, Kucheryavaya A Y, Levvey B J, Meiser B, Rossano J W, Chambers D C, Yusen R D, Stehlik J, International Society for Heart and Lung Transplantation. The Registry of the International Society for Heart and Lung Transplantation: Thirty-fourth Adult Heart Transplantation Report-2017; Focus Theme: Allograft ischemic time. *J Heart Lung Transplant.* 2017; 36:1037-1046.
8. Hershberger R E, Hedges D J, Morales A. Dilated cardiomyopathy: the complexity of a diverse genetic architecture. *Nat Rev Cardiol.* 2013; 10:531-547.
9. Kinnamon D D, Morales A, Bowen D J, Burke W, Hershberger R E, DCM Consortium*. Toward Genetics- Driven Early Intervention in Dilated Cardiomyopathy: Design and Implementation of the DCM Precision Medicine Study. *Circ Cardiovasc Genet* [Internet]. 2017; 10. Available from: dx.doi.org/10.1161/CIRCGENETICS.117.001826
10. Maatz H, Jens M, Liss M, Schafer S, Heinig M, Kirchner M, Adami E, Rintisch C, Dauksaite V, Radke M H, Selbach M, Barton P J R, Cook S A, Rajewsky N, Gotthardt M, Landthaler M, Hubner N. RNA-binding protein RBM20 represses splicing to orchestrate cardiac pre-mRNA processing. *J Clin Invest.* 2014; 124:3419-3430.
11. Beraldi R, Li X, Martinez Fernandez A, Reyes S, Secreto F, Terzic A, Olson T M, Nelson T J. Rbm20-deficient cardiogenesis reveals early disruption of RNA processing and sarcomere remodeling establishing a developmental etiology for dilated cardiomyopathy. *Hum Mol Genet.* 2014; 23:3779-3791.
12. Hershberger R E, Hedges D J, Morales A. Dilated cardiomyopathy: the complexity of a diverse genetic architecture. *Nat Rev Cardiol.* 2013; 10:531-547.
13. Chanavat V, Janin A, Millat G. A fast and cost-effective molecular diagnostic tool for genetic diseases involved in sudden cardiac death. *Clin Chim Acta.* 2016; 453:80-85.
14. Li D, Morales A, Gonzalez-Quintana J, Norton N, Siegfried J D, Hofmeyer M, Hershberger R E. Identification of Novel Mutations in RBM20 in Patients with Dilated Cardiomyopathy. *Clin Trans/Sci.* 2010; 3:90-97.
15. Brauch K M, Karst M L, Herron K J, de Andrade M, Pellikka P A, Rodeheffer R J, Michels V V, Olson T M. Mutations in ribonucleic acid binding protein gene cause familial dilated cardiomyopathy. *J Am Coll Cardiol.* 2009; 54:930-941.
16. Miller J N, Pearce D A. Nonsense-mediated decay in genetic disease: Friend or foe?*Mutation Research/Reviews in Mutation Research.* 2014; 762:52-64.
17. Burridge P W, Matsa E, Shukla P, Lin Z C, Churko J M, Ebert A D, Lan F, Diecke S, Huber B, Mordwinkin N M, Plews J R, Abilez O J, Cui B, Gold J D, Wu J C. Chemically defined generation of human cardiomyocytes. *Nat Methods.* 2014; 11:855-860.
18. Marks A R. Calcium and the heart: a question of life and death. *J Clin Invest.* 2003; 111:597-600.
19. Petryszak R, Burdett T, Fiorelli B, Fonseca N A, Gonzalez-Porta M, Hastings E, Huber W, Jupp S, Keays M, Kryvych N, McMurry J, Marioni J C, Malone J, Megy K, Rustici G, Tang A Y, Taubert J, Williams E, Mannion O, Parkinson H E, Brazma A. Expression Atlas update—a database of gene and transcript expression from microarray- and sequencing-based functional genomics experiments. *Nucleic Acids Res.* 2013; 42: D926-D932.
20. Colleoni S, Galli C, Gaspar J A, Meganathan K, Jagtap S, Hescheler J, Sachinidis A, Lazzari G. Development of a neural teratogenicity test based on human embryonic stem cells: response to retinoic acid exposure. *Toxicol Sci.* 2011; 124:370-377.
21. Guo W, Schafer S, Greaser M L, Radke M H, Liss M, Govindarajan T, Maatz H, Schulz H, Li S, Parrish A M, Dauksaite V, Vakeel P, Klaassen S, Gerull B, Thierfelder L, Regitz-Zagrosek V, Hacker T A, Saupe K W, Dec G W, Ellinor P T, MacRae C A, Spallek B, Fischer R, Perrot A, Ozcelik C, Saar K, Hubner N, Gotthardt M. RBM20, a gene for hereditary cardiomyopathy, regulates titin splicing. *Nat Med.* 2012; 18:766-773.
22. Li S, Guo W, Dewey C N, Greaser M L. Rbm20 regulates titin alternative splicing as a splicing repressor. *Nucleic Acids Res.* 2013; 41:2659-2672.
23. Hsiao J, Yuan T Y, Tsai M S, Lu C Y, Lin Y C, Lee M L, Lin S W, Chang F C, Liu Pimentel H, Olive C, Coito C, Shen G, Young M, Thorne T, Lawrence M, Magistri M, Faghihi M A, Khorkova O, Wahlestedt C. Upregulation of Haploinsufficient Gene Expression in the Brain by Targeting a Long Non-coding RNA Improves Seizure Phenotype in a Model of Dravet Syndrome. *EBioMedicine.* 2016; 9:257-277.
24. Zhang P, Huang A, Morales-Ruiz M, Starcher B C, Huang Y, Sessa W C, Niklason L E, Giordano F J. Engineered zinc-finger proteins can compensate genetic haploinsufficiency by transcriptional activation of the wild-type allele: application to Willams-Beuren syndrome and supravalvular aortic stenosis. *Hum Gene Ther.* 2012; 23:1186-1199.
25. Garg P, Oikonomopoulos A, Chen H, Li Y, Lam C K, Sallam K, Perez M, Lux R L, Sanguinetti M C, Wu J C. Genome Editing of Induced Pluripotent Stem Cells to Decipher Cardiac Channelopathy Variant. *J Am Coll Cardiol.* 2018; 72:62-75.
26. Murayama R, Kimura-Asami M, Togo-Ohno M, Yamasaki-Kato Y, Naruse T K, Yamamoto T, Hayashi T, Ai T, Spoonamore K G, Kovacs R J, Vatta M, Iizuka M, Saito M, Wani S, Hiraoka Y, Kimura A, Kuroyanagi H. Phosphorylation of the RSRSP stretch is critical for splicing regulation by RNA-Binding Motif Protein 20 (RBM20) through nuclear localization. *Sci Rep.* 2018; 8:8970.
27. Streckfuss-Bömeke K, Tiburcy M, Fomin A, Luo X, Li W, Fischer C, Ozcelik C, Perrot A, Sossalla S, Haas J, Vidal R O, Rebs S, Khadjeh S, Meder B, Bonn S, Linke W A, Zimmermann W-H, Hasenfuss G, Guan K. Severe DCM phenotype of patient harboring RBM20 mutation S635A can be modeled by patient-specific induced pluripotent stem cell-derived cardiomyocytes. *J Mol Cell Cardiol.* 2017; 113:9-21.
28. Wyles S P, Li X, Hrstka S C, Reyes S, Oommen S, Beraldi R, Edwards J, Terzic A, Olson T M, Nelson T J. Modeling structural and functional deficiencies of RBM20 familial dilated cardiomyopathy using human induced pluripotent stem cells. *Hum Mol Genet.* 2016; 25:254-265.
29. Kolanowski T J, Antos C L, Guan K. Making human cardiomyocytes up to date: Derivation, maturation state and perspectives. *Int J Cardiol.* 2017; 241:379-386.

Example 2

In Vivo Animal Model of RBM20-Deficient DCM

Figure 7A:
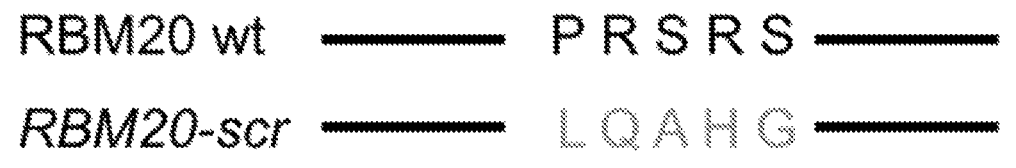
Figure 7B:
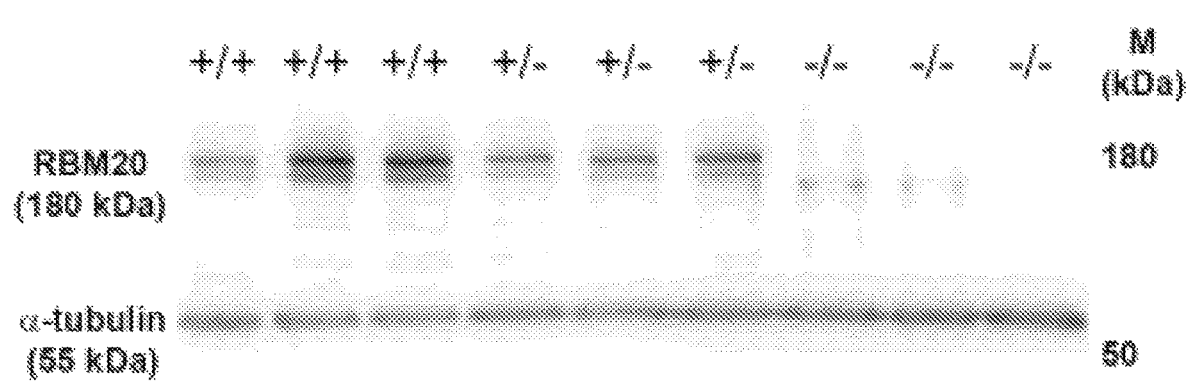

In this pilot study, five mice (Het mice)) with a heterozygous scramble mutation in RBM20 RS-domain (FIG. 7A) were used. This mutation likely leads to RBM20 functional knockout as protein expression in heterozygous mice was about half of the expression in WT mice and undetectable in homozygous mutant mice (FIG. 7B).

Two mice received vehicle control (sunflower oil: SF oil), and three received ATRA 50 mg/kg daily for 7 days by oral gavage delivery. All mice were 16.5-18.5 weeks old males (Table 1), and their well-being was monitored every day during the treatment period. No side effects were observed in mice during the study. After 7 days, the heart left ventricle (H) and leg quadriceps muscle (M) tissues were collected for further analyses of RBM20 expression.

TABLE 1

Animals involved in the first ATRA in vivo study (50 mg/kg, 7 days)

| Mouse | Age (weeks) | Age (days) | Sex | Cage | Treatment |
|---|---|---|---|---|---|
| Het/NT | | | | | |
| LST 027 153 | 17.5 | 122.5 | M | SLST-00138 | 100 µl SF oil |
| LST 027 152 | 17.5 | 122.5 | M | SLST-00148 | 100 µl SF oil |
| Het/ATRA | | | | | |
| LST 027 198 | 16.5 | 115.5 | M | SLST-00140 | 100 µl ATRA |
| LST 027 155 | 17.5 | 122.5 | M | SLST-00138 | 100 µl ATRA |
| LST 027 089 | 18.5 | 129.5 | M | SLST-00137 | 100 µl ATRA |

Figure 8A:
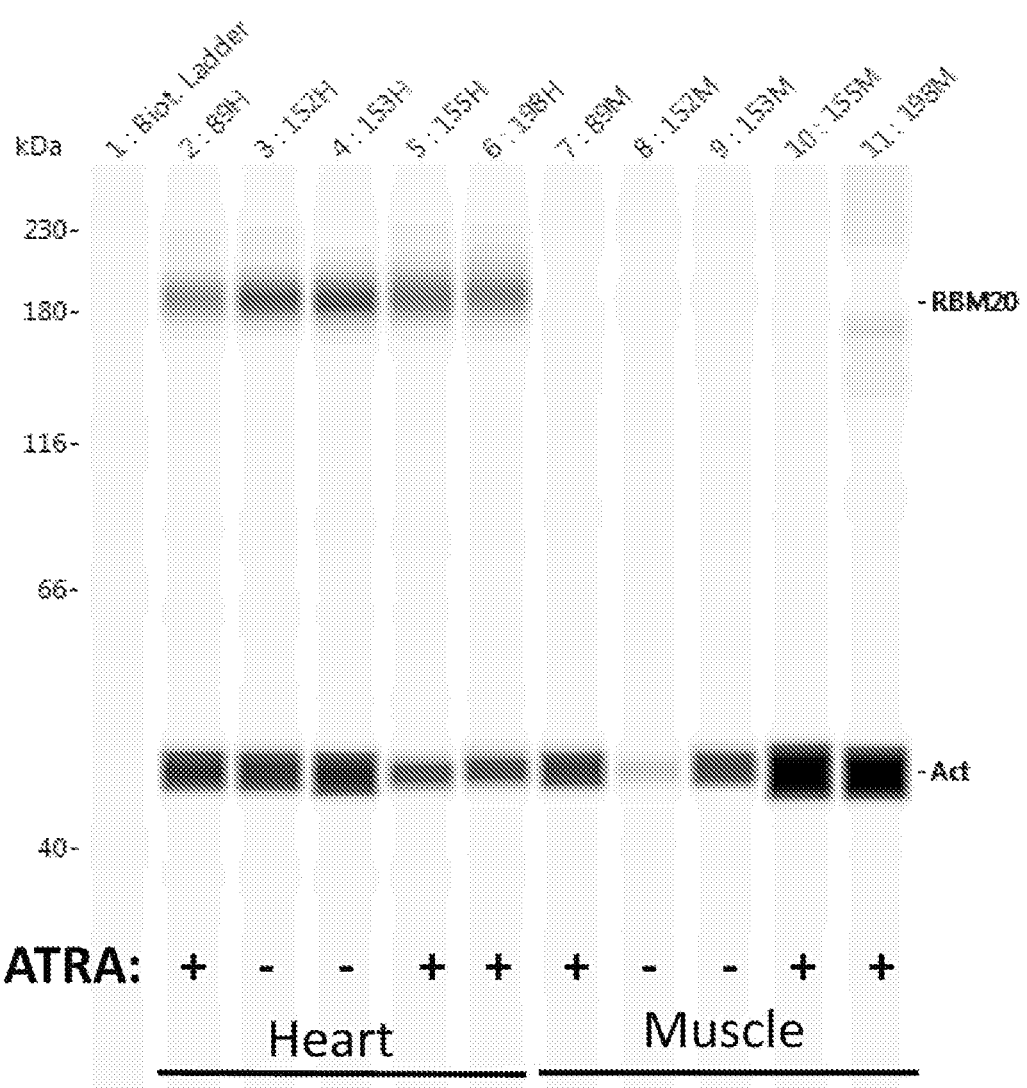
FIGS. 8A and 8B show effect of ATRA on RBM20 protein levels in mouse heart and muscle tissues.
Figure 8B:
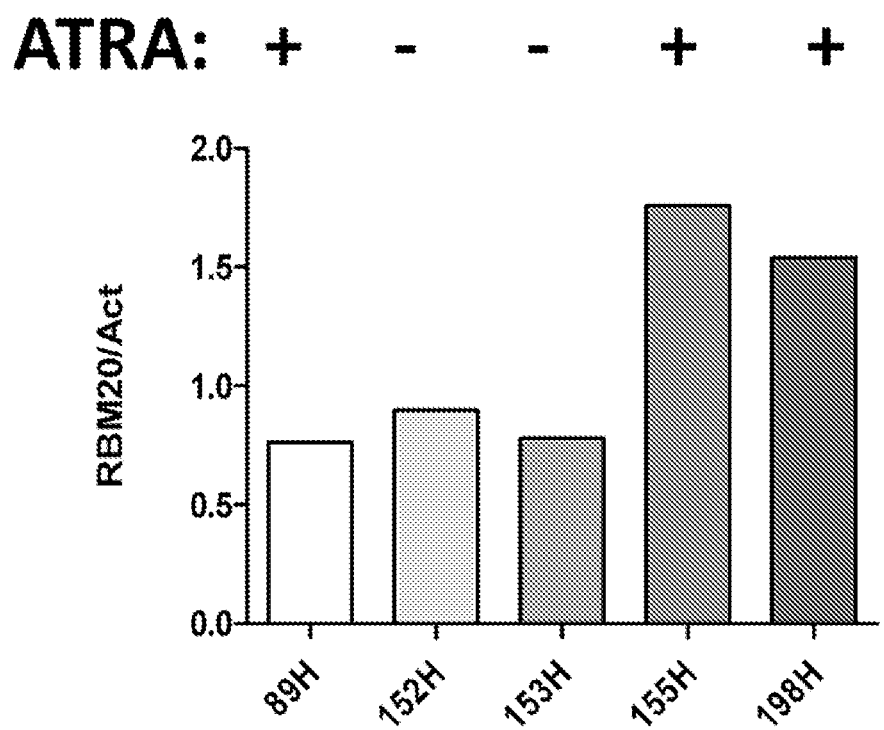
Figure 9A:
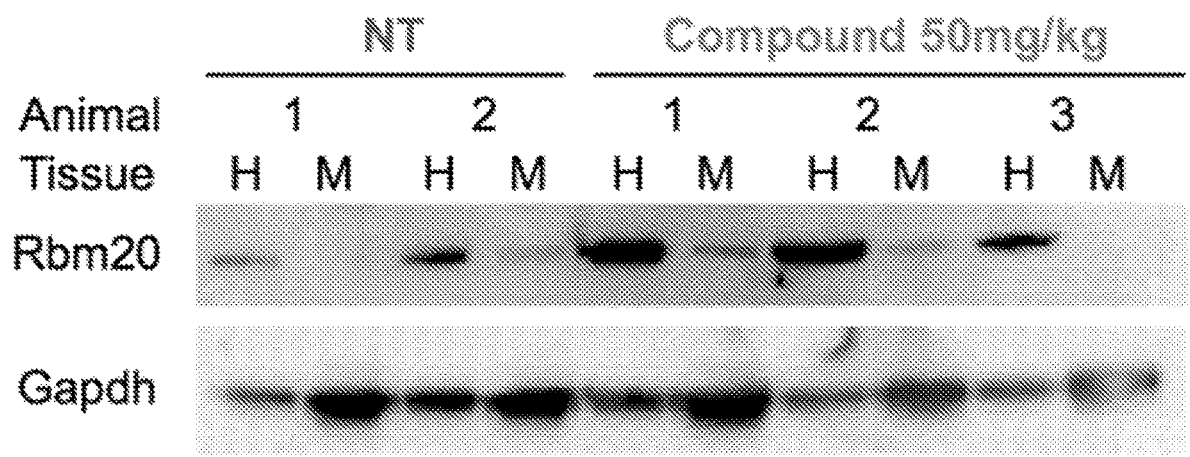
FIGS. 9A and 9B show the effects of ATRA on RBM20 and its downstream splicing targets (Titin, Camk2d) in mouse heart and skeletal muscle. Western blot (FIG. 9A) using anti-RBM20 and anti-GAPDH antibodies and quantification (FIG. 9B). ATRA treatment significantly increases RBM20 protein expression in heart but not in skeletal muscle. Compound is ATRA, NT is vehicle control. *−p<0.05, t-test.
Figure 9B:
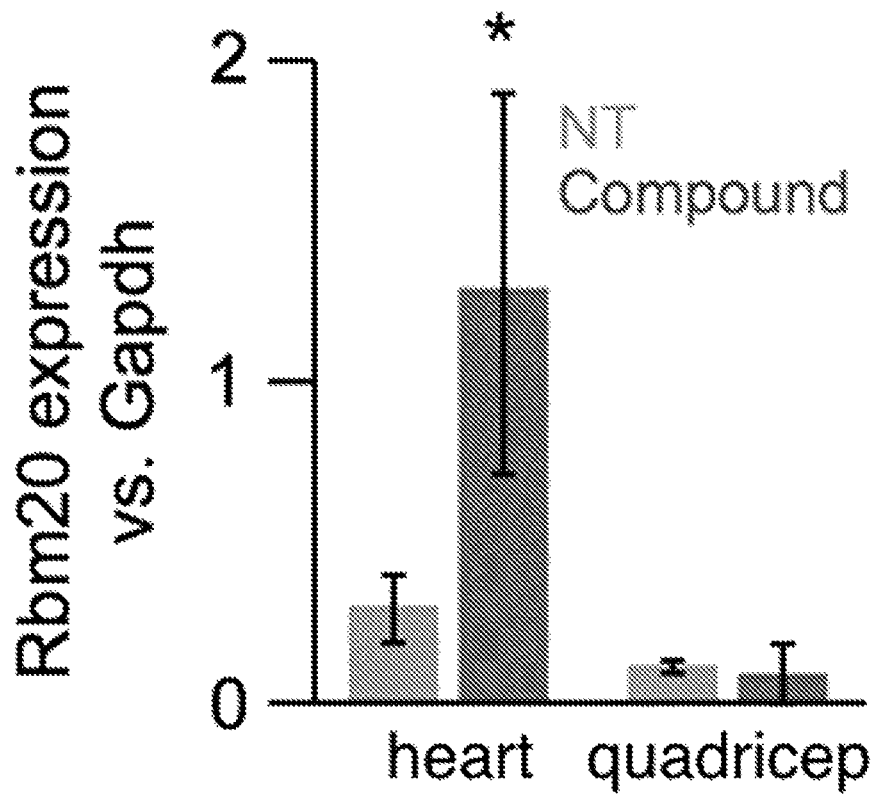

Upon ATRA treatment (50 mg/kg) for 7 days, RBM20 protein levels were increased in the hearts of Het mice. Western blot using capillary electrophoresis shows that in 2 out of 3 treated Het mice, RBM20 protein levels increased in the heart, but not in skeletal muscle tissues (FIG. 8A). This data was consistent with the Western blot results (FIG. 9A), showing significant upregulation of RBM20 in treated versus non-treated mice. GAPDH was used as loading control.

While the preferred embodiments of the invention have been illustrated and described, it will be appreciated that various changes can be made therein without departing from the spirit and scope of the invention.

What is claimed is:

1. A method of reducing RBM20-mediated splicing defects and increasing cardiomyocyte contractile capacity in a subject who has RBM20-deficient dilated cardiomyopathy (DCM), the method comprising administering an effective amount of all-trans retinoic acid (ATRA) to the subject, wherein the ATRA increases expression of RBM20 in the heart of the subject.

2. The method of claim 1, wherein the subject is heterozygous or homozygous for a P633L mutation in a RBM20 gene.

3. The method of claim 1, wherein the subject has deficient RBM20 expression.

4. The method of claim 1, wherein multiple cycles of treatment are administered to the subject.

5. The method of claim 1, wherein the ATRA is administered intermittently or according to a daily dosing regimen.

6. The method of claim 1, wherein the ATRA is administered orally, intravenously, intra-arterially, or intracardially.

7. The method of claim 1, wherein the ATRA is administered locally to the heart.

8. The method of claim 1, wherein the subject is human.

9. The method of claim 1, further comprising administering an angiotensin-converting-enzyme (ACE) inhibitor, a beta blocker, or a diuretic.

10. A method for diagnosing a genetic predisposition to developing RBM20-deficient dilated cardiomyopathy (DCM) and administering all-trans retinoic acid (ATRA) to a subject diagnosed with the genetic predisposition to developing the RBM20-deficient DCM, the method comprising:
   a) detecting whether the subject has a P633L mutation in RBM20;
   b) diagnosing the subject as having the genetic predisposition to developing RBM-29 dependent the RBM20-deficient DCM when the P633L mutation in the RBM20 is detected; and
   c) administering an effective amount of the ATRA to the subject diagnosed as having the genetic predisposition to developing the RBM20-deficient DCM, wherein RBM20-mediated splicing defects are reduced, and cardiomyocyte contractile capacity in the subject is increased.

11. The method of claim 10, wherein the subject is heterozygous or homozygous for the P633L mutation in the RBM20.

12. The method of claim 10, further comprising administering a therapeutically effective amount of an angiotensin-converting-enzyme (ACE) inhibitor, a beta blocker, or a diuretic to the subject diagnosed as having the genetic predisposition to developing the RBM20-deficient DCM, or implanting an artificial pacemaker or cardioverter-defibrillator in the subject diagnosed as having the genetic predisposition to developing the RBM20-deficient DCM.

13. The method of claim 10, wherein said detecting whether the subject has the P633L mutation comprises performing dynamic allele-specific hybridization (DASH), microarray analysis, Tetra-primer ARMS-PCR, a 5'-nuclease allelic discrimination assay; an allelic discrimination assay with Flap endonuclease (FEN), a Serial Invasive Signal Amplification Reaction (SISAR), an oligonucleotide ligase assay, restriction fragment length polymorphism (RFLP), single-strand conformation polymorphism, temperature gradient gel electrophoresis (TGGE), denaturing high performance liquid chromatography (DHPLC), sequencing, or an immunoassay.

14. The method of claim 10, wherein said detecting whether the subject has the P633L mutation comprises using an allele-specific probe that selectively hybridizes to a nucleic acid comprising an RBM20 gene sequence encoding the P633L mutation or using a set of allele-specific primers capable of selectively amplifying a nucleic acid comprising an RBM20 gene sequence encoding the P633L mutation.

15. The method of claim 10, further comprising detecting whether one or more other mutations in the RBM20 are present in at least one allele of an RMB20 gene in the subject's genome, wherein the one or more other mutations in the RBM20 are selected from the group consisting of R634Q, R634W, S635A, R636S, R636H, R636C, S637G, P638L, E913K, V535I, and R716Q, wherein said diagnosing the subject as having the genetic predisposition to developing the RBM20-deficient DCM comprises detecting the P633L mutation in the RBM20 in combination with the one or more other mutations in the RBM20 selected from the group consisting of R634Q, R634W, S635A, R636S, R636H, R636C, S637G, P638L, E913K, V535I, and R716Q.

* * * * *